(12) United States Patent
Robinson et al.

(10) Patent No.: US 12,409,310 B2
(45) Date of Patent: Sep. 9, 2025

(54) DESCENDING AORTA AND VENA CAVA BLOOD PUMPS

(71) Applicant: SHIFAMED HOLDINGS, LLC, Campbell, CA (US)

(72) Inventors: Janine Robinson, Half Moon Bay, CA (US); Daniel Hildebrand, Santa Cruz, CA (US); Michael Calomeni, San Jose, CA (US); Veronica Neiman, San Jose, CA (US); Tom Saul, Portland, OR (US); Robert Edesess, Campbell, CA (US)

(73) Assignee: SHIFAMED HOLDINGS, LLC, Campbell, CA (US)

( * ) Notice: Subject to any disclaimer, the term of this patent is extended or adjusted under 35 U.S.C. 154(b) by 355 days.

(21) Appl. No.: 17/784,758

(22) PCT Filed: Dec. 11, 2020

(86) PCT No.: PCT/US2020/064586
§ 371 (c)(1),
(2) Date: Jun. 13, 2022

(87) PCT Pub. No.: WO2021/119478
PCT Pub. Date: Jun. 17, 2021

(65) Prior Publication Data
US 2023/0001177 A1    Jan. 5, 2023

Related U.S. Application Data

(60) Provisional application No. 62/951,519, filed on Dec. 20, 2019, provisional application No. 62/946,927, filed on Dec. 11, 2019.

(51) Int. Cl.
*A61M 60/122* (2021.01)
*A61M 60/237* (2021.01)
*A61M 60/808* (2021.01)

(52) U.S. Cl.
CPC ........ *A61M 60/122* (2021.01); *A61M 60/808* (2021.01); *A61M 60/237* (2021.01)

(58) Field of Classification Search
CPC .............. A61M 60/122; A61M 60/808; A61M 60/237; A61M 60/33
See application file for complete search history.

(56) References Cited

U.S. PATENT DOCUMENTS

| | | |
|---|---|---|
| 1,061,107 A | 5/1913 | Nordmark |
| 1,596,933 A | 8/1926 | Kister |

(Continued)

FOREIGN PATENT DOCUMENTS

| | | |
|---|---|---|
| CA | 2352234 A1 | 6/2000 |
| CA | 2739899 C  | 5/2017 |

(Continued)

OTHER PUBLICATIONS

Calomeni et al.; U.S. Appl. No. 18/614,131 entitled "Intravascular blood pumps and methods of manufacture and use," filed Mar. 22, 2024.

(Continued)

*Primary Examiner* — Jonathan T Kuo
(74) *Attorney, Agent, or Firm* — Shay Glenn LLP

(57) ABSTRACT

Methods and devices for supporting circulation. The methods may include positioning a blood pump in the arterial vasculature or the venous vasculature. The methods may include positioning a pump portion of the blood pump in a descending aorta, an inferior vena cava, a renal artery, and/or a renal vein. The methods include delivering a pump portion of a blood pump to a target location and rotating one or more impellers to move blood through the pump portion.

18 Claims, 5 Drawing Sheets

(56) References Cited

U.S. PATENT DOCUMENTS

| | | |
|---|---|---|
| 3,152,618 A | 10/1964 | Rothermel et al. |
| 3,175,555 A | 3/1965 | Ling |
| 3,178,833 A | 4/1965 | Gulbransen, Jr. |
| 3,208,448 A | 9/1965 | Woodward |
| 3,233,609 A | 2/1966 | Leucci |
| 3,421,497 A | 1/1969 | Chesnut |
| 3,502,412 A | 3/1970 | Burns |
| 3,504,662 A | 4/1970 | Jones |
| 3,505,987 A | 4/1970 | Heilman |
| 3,568,659 A | 3/1971 | Karnegis |
| 3,693,612 A | 9/1972 | Donahoe et al. |
| 3,734,648 A | 5/1973 | Nielson |
| 3,774,243 A | 11/1973 | Ng et al. |
| 3,837,922 A | 9/1974 | Ng et al. |
| 3,841,837 A | 10/1974 | Kitrilakis et al. |
| 3,860,968 A | 1/1975 | Shapiro |
| 3,919,722 A | 11/1975 | Harmison |
| 4,015,590 A | 4/1977 | Normann |
| 4,037,984 A | 7/1977 | Rafferty et al. |
| 4,046,137 A | 9/1977 | Curless et al. |
| 4,058,857 A | 11/1977 | Runge et al. |
| 4,093,726 A | 6/1978 | Winn et al. |
| 4,135,253 A | 1/1979 | Reich et al. |
| 4,142,845 A | 3/1979 | Lepp et al. |
| 4,173,796 A | 11/1979 | Jarvik |
| 4,190,047 A | 2/1980 | Jacobsen et al. |
| 4,255,821 A | 3/1981 | Carol et al. |
| 4,289,141 A | 9/1981 | Cormier |
| 4,310,930 A | 1/1982 | Goldowsky |
| 4,311,133 A | 1/1982 | Robinson |
| 4,328,806 A | 5/1982 | Cooper |
| 4,370,983 A | 2/1983 | Lichtenstein |
| 4,381,005 A | 4/1983 | Bujan |
| 4,381,567 A | 5/1983 | Robinson et al. |
| 4,382,199 A | 5/1983 | Isaacson |
| 4,389,737 A | 6/1983 | Robinson et al. |
| 4,397,049 A | 8/1983 | Robinson et al. |
| 4,407,304 A | 10/1983 | Lieber et al. |
| 4,506,658 A | 3/1985 | Casile |
| 4,515,589 A | 5/1985 | Austin et al. |
| 4,522,195 A | 6/1985 | Schiff |
| 4,524,466 A | 6/1985 | Hall et al. |
| 4,551,073 A | 11/1985 | Schwab |
| 4,576,606 A | 3/1986 | Pol et al. |
| 4,585,004 A | 4/1986 | Brownlee |
| 4,585,007 A | 4/1986 | Uchigaki et al. |
| 4,599,081 A | 7/1986 | Cohen |
| 4,600,405 A | 7/1986 | Zibelin |
| 4,623,350 A | 11/1986 | Lapeyre et al. |
| 4,625,712 A | 12/1986 | Wampler |
| 4,652,265 A | 3/1987 | McDougall |
| 4,662,358 A | 5/1987 | Farrar et al. |
| 4,666,598 A | 5/1987 | Heath et al. |
| 4,675,361 A | 6/1987 | Ward |
| 4,685,910 A | 8/1987 | Schweizer |
| 4,726,379 A | 2/1988 | Altman et al. |
| 4,753,221 A | 6/1988 | Kensey et al. |
| 4,767,289 A | 8/1988 | Parrott et al. |
| 4,771,777 A | 9/1988 | Horzewski et al. |
| 4,779,614 A | 10/1988 | Moise |
| 4,782,817 A | 11/1988 | Singh et al. |
| 4,785,795 A | 11/1988 | Singh |
| 4,802,650 A | 2/1989 | Stricker |
| 4,818,186 A | 4/1989 | Pastrone et al. |
| 4,826,481 A | 5/1989 | Sacks et al. |
| 4,846,152 A | 7/1989 | Wampler et al. |
| 4,846,831 A | 7/1989 | Skillin |
| 4,850,957 A | 7/1989 | Summers |
| 4,888,009 A | 12/1989 | Lederman et al. |
| 4,888,011 A | 12/1989 | Kung et al. |
| 4,902,272 A | 2/1990 | Milder et al. |
| 4,907,592 A | 3/1990 | Harper |
| 4,908,012 A | 3/1990 | Moise et al. |
| 4,919,647 A | 4/1990 | Nash |
| 4,936,759 A | 6/1990 | Clausen et al. |
| 4,961,738 A | 10/1990 | Mackin |
| 4,976,683 A | 12/1990 | Gauthier et al. |
| 4,995,857 A | 2/1991 | Arnold |
| 5,026,367 A | 6/1991 | Leckrone et al. |
| D318,113 S | 7/1991 | Moutafis et al. |
| 5,045,051 A | 9/1991 | Milder et al. |
| 5,046,503 A | 9/1991 | Schneiderman |
| 5,047,147 A | 9/1991 | Chevallet et al. |
| 5,049,134 A | 9/1991 | Golding et al. |
| 5,061,256 A | 10/1991 | Wampler |
| 5,084,064 A | 1/1992 | Barak et al. |
| 5,089,016 A | 2/1992 | Millner et al. |
| 5,090,957 A | 2/1992 | Moutafis et al. |
| 5,092,844 A | 3/1992 | Schwartz et al. |
| 5,092,879 A | 3/1992 | Jarvik |
| 5,112,200 A | 5/1992 | Isaacson et al. |
| 5,112,292 A | 5/1992 | Hwang et al. |
| 5,114,399 A | 5/1992 | Kovalcheck |
| 5,116,305 A | 5/1992 | Milder et al. |
| 5,139,517 A | 8/1992 | Corral |
| 5,145,333 A | 9/1992 | Smith |
| 5,147,281 A | 9/1992 | Thornton et al. |
| 5,171,264 A | 12/1992 | Merrill |
| 5,180,378 A | 1/1993 | Kung et al. |
| 5,192,314 A | 3/1993 | Daskalakis |
| 5,200,050 A | 4/1993 | Ivory et al. |
| 5,205,721 A | 4/1993 | Isaacson |
| 5,211,546 A | 5/1993 | Isaacson et al. |
| 5,261,411 A | 11/1993 | Hughes |
| 5,270,005 A | 12/1993 | Raible |
| 5,287,858 A | 2/1994 | Hammerslag et al. |
| 5,300,111 A | 4/1994 | Panton et al. |
| 5,300,112 A | 4/1994 | Barr |
| 5,314,418 A | 5/1994 | Takano et al. |
| 5,322,413 A | 6/1994 | Vescovini et al. |
| 5,326,344 A | 7/1994 | Bramm et al. |
| 5,363,856 A | 11/1994 | Hughes et al. |
| 5,397,349 A | 3/1995 | Kolff et al. |
| 5,399,074 A | 3/1995 | Nose et al. |
| 5,405,251 A | 4/1995 | Sipin |
| 5,441,636 A | 8/1995 | Chevallet et al. |
| 5,443,504 A | 8/1995 | Hill |
| 5,486,192 A | 1/1996 | Walinsky et al. |
| 5,487,727 A | 1/1996 | Snider et al. |
| 5,507,629 A | 4/1996 | Jarvik |
| 5,507,795 A | 4/1996 | Chiang et al. |
| 5,510,267 A | 4/1996 | Marshall |
| 5,512,042 A | 4/1996 | Montoya et al. |
| 5,531,789 A | 7/1996 | Yamazaki et al. |
| 5,628,731 A | 5/1997 | Dodge et al. |
| 5,630,835 A | 5/1997 | Brownlee |
| 5,643,172 A | 7/1997 | Kung et al. |
| 5,643,215 A | 7/1997 | Fuhrman et al. |
| 5,653,696 A | 8/1997 | Shiber |
| 5,662,643 A | 9/1997 | Kung et al. |
| 5,676,526 A | 10/1997 | Kuwana et al. |
| 5,683,231 A | 11/1997 | Nakazawa et al. |
| 5,702,365 A | 12/1997 | King |
| 5,713,730 A | 2/1998 | Nose et al. |
| 5,735,892 A | 4/1998 | Myers et al. |
| 5,749,839 A | 5/1998 | Kovacs |
| 5,749,855 A | 5/1998 | Reitan |
| 5,751,125 A | 5/1998 | Weiss |
| 5,759,148 A | 6/1998 | Sipin |
| 5,766,207 A | 6/1998 | Potter et al. |
| 5,776,096 A | 7/1998 | Fields |
| 5,800,138 A | 9/1998 | Merce Vives |
| 5,800,457 A | 9/1998 | Gelbfish |
| 5,803,720 A | 9/1998 | Ohara et al. |
| 5,814,076 A | 9/1998 | Brownlee |
| 5,814,102 A | 9/1998 | Guldner et al. |
| 5,851,174 A | 12/1998 | Jarvik et al. |
| 5,888,241 A | 3/1999 | Jarvik |
| 5,906,579 A | 5/1999 | Vander Salm et al. |
| 5,910,124 A | 6/1999 | Rubin |
| 5,919,369 A | 7/1999 | Ash |
| 5,941,813 A | 8/1999 | Sievers et al. |
| 5,957,672 A | 9/1999 | Aber |
| 5,964,694 A | 10/1999 | Siess et al. |

(56) References Cited

U.S. PATENT DOCUMENTS

| | | |
|---|---|---|
| 5,984,893 A | 11/1999 | Ward |
| 6,007,478 A | 12/1999 | Siess et al. |
| 6,013,058 A | 1/2000 | Prosl et al. |
| 6,022,363 A | 2/2000 | Walker et al. |
| 6,030,336 A | 2/2000 | Franchi |
| 6,042,347 A | 3/2000 | Scholl et al. |
| 6,053,943 A | 4/2000 | Edwin et al. |
| 6,066,085 A | 5/2000 | Heilman et al. |
| 6,066,152 A | 5/2000 | Strauss et al. |
| 6,068,588 A | 5/2000 | Goldowsky |
| 6,071,093 A | 6/2000 | Hart |
| 6,071,258 A | 6/2000 | Dalke et al. |
| 6,082,105 A | 7/2000 | Miyata |
| 6,101,406 A | 8/2000 | Hacker et al. |
| 6,106,509 A | 8/2000 | Loubser |
| 6,113,536 A | 9/2000 | Hosn et al. |
| 6,117,130 A | 9/2000 | Kung |
| 6,117,390 A | 9/2000 | Corey |
| 6,120,537 A | 9/2000 | Wampler |
| 6,123,659 A | 9/2000 | Le Blanc et al. |
| 6,123,726 A | 9/2000 | Mori et al. |
| 6,129,660 A | 10/2000 | Nakazeki et al. |
| 6,136,025 A | 10/2000 | Barbut et al. |
| 6,139,487 A | 10/2000 | Siess |
| 6,142,752 A | 11/2000 | Akamatsu et al. |
| 6,146,771 A | 11/2000 | Wirt et al. |
| 6,149,683 A | 11/2000 | Lancisi et al. |
| 6,152,704 A | 11/2000 | Aboul Hosn et al. |
| 6,155,969 A | 12/2000 | Schima et al. |
| 6,176,848 B1 | 1/2001 | Rau et al. |
| 6,180,058 B1 | 1/2001 | Lindsay |
| 6,197,055 B1 | 3/2001 | Matthews |
| 6,197,289 B1 | 3/2001 | Wirt et al. |
| 6,210,133 B1 | 4/2001 | Aboul Hosn et al. |
| 6,210,318 B1 | 4/2001 | Lederman |
| 6,228,023 B1 | 5/2001 | Zaslavsky et al. |
| 6,236,883 B1 | 5/2001 | Ciaccio et al. |
| 6,254,359 B1 | 7/2001 | Aber |
| 6,270,831 B2 | 8/2001 | Kumar et al. |
| 6,273,861 B1 | 8/2001 | Bates et al. |
| 6,283,949 B1 | 9/2001 | Roorda |
| 6,287,319 B1 | 9/2001 | Aboul Hosn et al. |
| 6,290,685 B1 | 9/2001 | Insley et al. |
| 6,312,462 B1 | 11/2001 | McDermott et al. |
| 6,314,322 B1 | 11/2001 | Rosenberg |
| 6,319,231 B1 | 11/2001 | Andrulitis |
| 6,361,292 B1 | 3/2002 | Chang et al. |
| 6,361,501 B1 | 3/2002 | Amano et al. |
| 6,364,833 B1 | 4/2002 | Valerio et al. |
| 6,398,715 B1 | 6/2002 | Magovern et al. |
| 6,400,991 B1 | 6/2002 | Kung |
| 6,406,267 B1 | 6/2002 | Mondiere |
| 6,406,422 B1 | 6/2002 | Landesberg |
| 6,419,657 B1 | 7/2002 | Pacetti |
| 6,422,990 B1 | 7/2002 | Prem |
| 6,432,136 B1 | 8/2002 | Weiss et al. |
| 6,443,944 B1 | 9/2002 | Doshi et al. |
| 6,443,983 B1 | 9/2002 | Nagyszalanczy et al. |
| 6,445,956 B1 | 9/2002 | Laird et al. |
| 6,447,265 B1 | 9/2002 | Antaki et al. |
| 6,447,266 B2 | 9/2002 | Antaki et al. |
| 6,447,441 B1 | 9/2002 | Yu et al. |
| 6,497,680 B1 | 12/2002 | Holst et al. |
| 6,503,224 B1 | 1/2003 | Forman et al. |
| 6,503,450 B1 | 1/2003 | Afzal et al. |
| 6,508,787 B2 | 1/2003 | Erbel et al. |
| 6,508,806 B1 | 1/2003 | Hoste |
| 6,527,699 B1 | 3/2003 | Goldowsky |
| 6,533,716 B1 | 3/2003 | Schmitz-Rode et al. |
| 6,533,724 B2 | 3/2003 | McNair |
| 6,537,315 B2 | 3/2003 | Yamazaki et al. |
| 6,540,658 B1 | 4/2003 | Fasciano et al. |
| 6,540,659 B1 | 4/2003 | Milbocker |
| 6,544,543 B1 | 4/2003 | Mandrusov et al. |
| 6,547,716 B1 | 4/2003 | Milbocker |
| 6,562,022 B2 | 5/2003 | Hoste et al. |
| 6,572,529 B2 | 6/2003 | Wilk |
| 6,572,534 B1 | 6/2003 | Milbocker et al. |
| 6,595,943 B1 | 7/2003 | Burbank |
| 6,602,182 B1 | 8/2003 | Milbocker |
| 6,616,596 B1 | 9/2003 | Milbocker |
| 6,620,120 B2 | 9/2003 | Landry et al. |
| 6,623,420 B2 | 9/2003 | Reich et al. |
| 6,626,821 B1 | 9/2003 | Kung et al. |
| 6,626,889 B1 | 9/2003 | Simpson et al. |
| 6,626,935 B1 | 9/2003 | Ainsworth et al. |
| 6,632,215 B1 | 10/2003 | Lemelson |
| 6,635,083 B1 | 10/2003 | Cheng et al. |
| 6,656,220 B1 | 12/2003 | Gomez et al. |
| 6,669,624 B2 | 12/2003 | Frazier |
| 6,669,662 B1 | 12/2003 | Webler |
| 6,676,679 B1 | 1/2004 | Mueller et al. |
| 6,685,696 B2 | 2/2004 | Fleischhacker et al. |
| 6,688,869 B1 | 2/2004 | Simonds |
| 6,699,231 B1 | 3/2004 | Sterman et al. |
| 6,709,382 B1 | 3/2004 | Horner |
| 6,712,844 B2 | 3/2004 | Pacetti |
| 6,730,102 B1 | 5/2004 | Burdulis et al. |
| 6,746,416 B2 | 6/2004 | Hubbard et al. |
| 6,749,615 B2 | 6/2004 | Burdulis et al. |
| 6,769,871 B2 | 8/2004 | Yamazaki |
| 6,790,171 B1 | 9/2004 | Gründeman et al. |
| 6,811,749 B2 | 11/2004 | Lindsay |
| 6,821,295 B1 | 11/2004 | Farrar |
| 6,837,890 B1 | 1/2005 | Chludzinski et al. |
| 6,846,296 B1 | 1/2005 | Milbocker et al. |
| 6,866,650 B2 | 3/2005 | Stevens et al. |
| 6,879,126 B2 | 4/2005 | Paden et al. |
| 6,884,210 B2 | 4/2005 | Nose et al. |
| 6,908,280 B2 | 6/2005 | Yamazaki |
| 6,908,435 B1 | 6/2005 | Mueller et al. |
| 6,929,632 B2 | 8/2005 | Nita et al. |
| 6,929,660 B1 | 8/2005 | Ainsworth et al. |
| 6,942,672 B2 | 9/2005 | Heilman et al. |
| 6,945,978 B1 | 9/2005 | Hyde |
| 6,949,066 B2 | 9/2005 | Beamson et al. |
| 6,969,345 B2 | 11/2005 | Jassawalla et al. |
| 6,981,942 B2 | 1/2006 | Khaw et al. |
| 7,022,100 B1 | 4/2006 | Hosn et al. |
| 7,025,742 B2 | 4/2006 | Rubenstein et al. |
| 7,027,875 B2 | 4/2006 | Siess et al. |
| 7,029,483 B2 | 4/2006 | Schwartz |
| 7,037,253 B2 | 5/2006 | French et al. |
| 7,048,747 B2 | 5/2006 | Arcia et al. |
| 7,074,018 B2 | 7/2006 | Chang |
| 7,108,652 B2 | 9/2006 | Stenberg et al. |
| 7,118,525 B2 | 10/2006 | Coleman et al. |
| 7,122,151 B2 | 10/2006 | Reeder et al. |
| 7,125,376 B2 | 10/2006 | Viole et al. |
| 7,126,310 B1 | 10/2006 | Barron |
| 7,150,711 B2 | 12/2006 | Nüsser et al. |
| 7,155,291 B2 | 12/2006 | Zarinetchi et al. |
| 7,172,551 B2 | 2/2007 | Leasure |
| 7,189,260 B2 | 3/2007 | Horvath et al. |
| 7,220,275 B2 | 5/2007 | Davidson et al. |
| 7,229,258 B2 | 6/2007 | Wood et al. |
| 7,229,402 B2 | 6/2007 | Diaz et al. |
| 7,238,151 B2 | 7/2007 | Frazier |
| 7,244,224 B2 | 7/2007 | Tsukahara et al. |
| 7,247,166 B2 | 7/2007 | Pienknagura |
| 7,303,581 B2 | 12/2007 | Peralta |
| 7,331,972 B1 | 2/2008 | Cox |
| 7,331,987 B1 | 2/2008 | Cox |
| 7,361,726 B2 | 4/2008 | Pacetti et al. |
| 7,377,927 B2 | 5/2008 | Burdulis et al. |
| 7,392,077 B2 | 6/2008 | Mueller et al. |
| 7,393,181 B2 | 7/2008 | McBride et al. |
| 7,396,327 B2 | 7/2008 | Morello |
| 7,479,102 B2 | 1/2009 | Jarvik |
| 7,520,850 B2 | 4/2009 | Brockway |
| 7,524,277 B1 | 4/2009 | Wang et al. |
| 7,541,000 B2 | 6/2009 | Stringer et al. |
| 7,544,160 B2 | 6/2009 | Gross |
| 7,547,391 B2 | 6/2009 | Petrie |

(56) References Cited

U.S. PATENT DOCUMENTS

| | | |
|---|---|---|
| 7,585,322 B2 | 9/2009 | Azzolina |
| 7,588,530 B2 | 9/2009 | Heilman et al. |
| 7,588,549 B2 | 9/2009 | Eccleston |
| 7,591,199 B2 | 9/2009 | Weldon et al. |
| 7,611,478 B2 | 11/2009 | Lucke et al. |
| 7,628,756 B2 | 12/2009 | Hacker et al. |
| 7,713,259 B2 | 5/2010 | Gosiengfiao et al. |
| RE41,394 E | 6/2010 | Bugge et al. |
| 7,731,664 B1 | 6/2010 | Millar |
| 7,736,296 B2 | 6/2010 | Siess et al. |
| 7,736,375 B2 | 6/2010 | Crow |
| 7,758,492 B2 | 7/2010 | Weatherbee |
| 7,776,991 B2 | 8/2010 | Pacetti et al. |
| 7,780,628 B1 | 8/2010 | Keren et al. |
| 7,794,419 B2 | 9/2010 | Paolini et al. |
| 7,794,743 B2 | 9/2010 | Simhambhatla et al. |
| 7,819,834 B2 | 10/2010 | Paul |
| 7,828,710 B2 | 11/2010 | Shifflette |
| 7,833,239 B2 | 11/2010 | Nash |
| 7,841,976 B2 | 11/2010 | McBride et al. |
| 7,850,594 B2 | 12/2010 | Sutton et al. |
| 7,862,501 B2 | 1/2011 | Woodard |
| 7,878,967 B1 | 2/2011 | Khanal |
| 7,914,436 B1 | 3/2011 | Kung |
| 7,922,657 B2 | 4/2011 | Gillinov et al. |
| 7,942,804 B2 | 5/2011 | Khaw |
| 7,963,905 B2 | 6/2011 | Salmonsen et al. |
| 7,972,122 B2 | 7/2011 | LaRose et al. |
| 7,972,291 B2 | 7/2011 | Ibragimov |
| 7,985,442 B2 | 7/2011 | Gong |
| 7,988,728 B2 | 8/2011 | Ayre |
| 7,993,259 B2 | 8/2011 | Kang et al. |
| 7,993,260 B2 | 8/2011 | Bolling |
| 7,993,358 B2 | 8/2011 | O'Brien |
| 7,998,054 B2 | 8/2011 | Bolling |
| 7,998,190 B2 | 8/2011 | Gharib et al. |
| 8,012,079 B2 | 9/2011 | Delgado |
| 8,012,194 B2 | 9/2011 | Edwin et al. |
| 8,012,508 B2 | 9/2011 | Ludwig |
| 8,029,728 B2 | 10/2011 | Lindsay |
| 8,034,098 B1 | 10/2011 | Callas et al. |
| 8,048,442 B1 | 11/2011 | Hossainy et al. |
| 8,052,749 B2 | 11/2011 | Salahieh et al. |
| 8,070,742 B2 | 12/2011 | Woo |
| 8,070,804 B2 | 12/2011 | Hyde et al. |
| 8,075,472 B2 | 12/2011 | Zilbershlag et al. |
| 8,079,948 B2 | 12/2011 | Shifflette |
| 8,083,726 B1 | 12/2011 | Wang |
| 8,123,669 B2 | 2/2012 | Siess et al. |
| 8,123,674 B2 | 2/2012 | Kuyava |
| 8,133,272 B2 | 3/2012 | Hyde |
| RE43,299 E | 4/2012 | Siess |
| 8,152,035 B2 | 4/2012 | Eart |
| 8,152,845 B2 | 4/2012 | Bourque |
| 8,153,083 B2 | 4/2012 | Briggs |
| 8,157,719 B1 | 4/2012 | Ainsworth et al. |
| 8,157,721 B2 | 4/2012 | Sugiura |
| 8,157,758 B2 | 4/2012 | Pecor et al. |
| 8,158,062 B2 | 4/2012 | Dykes et al. |
| 8,162,021 B2 | 4/2012 | Tomasetti et al. |
| 8,167,589 B2 | 5/2012 | Hidaka et al. |
| 8,172,783 B1 | 5/2012 | Ray |
| 8,177,750 B2 | 5/2012 | Steinbach et al. |
| 8,187,324 B2 | 5/2012 | Webler et al. |
| 8,197,463 B2 | 6/2012 | Intoccia |
| 8,210,829 B2 | 7/2012 | Horvath et al. |
| 8,241,199 B2 | 8/2012 | Maschke |
| 8,257,258 B2 | 9/2012 | Zocchi |
| 8,257,375 B2 | 9/2012 | Maschke |
| 8,266,943 B2 | 9/2012 | Miyakoshi et al. |
| D669,585 S | 10/2012 | Bourque |
| 8,277,476 B2 | 10/2012 | Taylor et al. |
| 8,282,359 B2 | 10/2012 | Ayre et al. |
| 8,292,908 B2 | 10/2012 | Nieman et al. |
| D671,646 S | 11/2012 | Bourque et al. |
| 8,303,482 B2 | 11/2012 | Schima et al. |
| 8,323,173 B2 | 12/2012 | Benkowski et al. |
| 8,323,203 B2 | 12/2012 | Thornton |
| 8,328,750 B2 | 12/2012 | Peters et al. |
| 8,329,114 B2 | 12/2012 | Temple |
| 8,329,158 B2 | 12/2012 | Hossainy et al. |
| 8,366,599 B2 | 2/2013 | Tansley et al. |
| 8,372,137 B2 | 2/2013 | Pienknagura |
| 8,377,033 B2 | 2/2013 | Basu et al. |
| 8,377,083 B2 | 2/2013 | Mauch et al. |
| 8,382,695 B1 | 2/2013 | Patel |
| 8,388,565 B2 | 3/2013 | Shifflette |
| 8,388,649 B2 | 3/2013 | Woodard et al. |
| 8,419,609 B2 | 4/2013 | Shambaugh et al. |
| 8,419,944 B2 | 4/2013 | Alkanhal |
| 8,439,909 B2 | 5/2013 | Wang et al. |
| 8,449,444 B2 | 5/2013 | Poirier |
| 8,454,683 B2 | 6/2013 | Rafiee et al. |
| 8,485,961 B2 | 7/2013 | Campbell et al. |
| 8,496,874 B2 | 7/2013 | Gellman et al. |
| 8,500,620 B2 | 8/2013 | Lu et al. |
| 8,506,471 B2 | 8/2013 | Bourque |
| 8,535,211 B2 | 9/2013 | Campbell et al. |
| 8,535,212 B2 | 9/2013 | Robert |
| 8,538,515 B2 | 9/2013 | Atanasoska et al. |
| 8,545,382 B2 | 10/2013 | Suzuki et al. |
| 8,545,447 B2 | 10/2013 | Demarais et al. |
| 8,562,509 B2 | 10/2013 | Bates |
| 8,568,289 B2 | 10/2013 | Mazur |
| 8,579,858 B2 | 11/2013 | Reitan et al. |
| 8,579,967 B2 | 11/2013 | Webler et al. |
| 8,585,572 B2 | 11/2013 | Mehmanesh |
| 8,586,527 B2 | 11/2013 | Singh |
| 8,591,393 B2 | 11/2013 | Walters et al. |
| 8,591,394 B2 | 11/2013 | Peters et al. |
| 8,591,449 B2 | 11/2013 | Hudson |
| 8,591,538 B2 | 11/2013 | Gellman |
| 8,591,539 B2 | 11/2013 | Gellman |
| D696,769 S | 12/2013 | Schenck et al. |
| 8,597,170 B2 | 12/2013 | Walters et al. |
| 8,608,661 B1 | 12/2013 | Mandrusov et al. |
| 8,613,777 B2 | 12/2013 | Siess et al. |
| 8,613,892 B2 | 12/2013 | Stafford |
| 8,617,239 B2 | 12/2013 | Reitan |
| 8,631,680 B2 | 1/2014 | Fleischli et al. |
| 8,632,449 B2 | 1/2014 | Masuzawa et al. |
| 8,641,594 B2 | 2/2014 | LaRose et al. |
| 8,657,871 B2 | 2/2014 | Limon |
| 8,657,875 B2 | 2/2014 | Kung et al. |
| 8,668,473 B2 | 3/2014 | LaRose et al. |
| 8,684,903 B2 | 4/2014 | Nour |
| 8,690,749 B1 | 4/2014 | Nunez |
| 8,690,823 B2 | 4/2014 | Yribarren et al. |
| 8,697,058 B2 | 4/2014 | Basu et al. |
| 8,708,948 B2 | 4/2014 | Consigny et al. |
| 8,715,151 B2 | 5/2014 | Poirier |
| 8,715,156 B2 | 5/2014 | Jayaraman |
| 8,715,707 B2 | 5/2014 | Hossainy et al. |
| 8,721,516 B2 | 5/2014 | Scheckel |
| 8,721,517 B2 | 5/2014 | Zeng et al. |
| 8,734,331 B2 | 5/2014 | Evans et al. |
| 8,734,508 B2 | 5/2014 | Hastings et al. |
| 8,739,727 B2 | 6/2014 | Austin et al. |
| 8,740,920 B2 | 6/2014 | Goldfarb et al. |
| 8,741,287 B2 | 6/2014 | Brophy et al. |
| 8,758,388 B2 | 6/2014 | Pah |
| 8,766,788 B2 | 7/2014 | D'Ambrosio |
| 8,777,832 B1 | 7/2014 | Wang et al. |
| 8,790,399 B2 | 7/2014 | Frazier et al. |
| 8,795,576 B2 | 8/2014 | Tao et al. |
| 8,814,543 B2 | 8/2014 | Liebing |
| 8,814,776 B2 | 8/2014 | Hastie et al. |
| 8,814,933 B2 | 8/2014 | Siess |
| 8,815,274 B2 | 8/2014 | DesNoyer et al. |
| 8,821,366 B2 | 9/2014 | Farnan et al. |
| 8,837,096 B2 | 9/2014 | Seebruch |
| 8,840,539 B2 | 9/2014 | Zilbershlag |
| 8,840,566 B2 | 9/2014 | Seibel et al. |
| 8,849,398 B2 | 9/2014 | Evans |

(56) References Cited

U.S. PATENT DOCUMENTS

| | | |
|---|---|---|
| 8,862,232 B2 | 10/2014 | Zarinetchi et al. |
| 8,864,642 B2 | 10/2014 | Scheckel |
| 8,876,685 B2 | 11/2014 | Crosby et al. |
| 8,882,744 B2 | 11/2014 | Dormanen et al. |
| 8,888,675 B2 | 11/2014 | Stankus et al. |
| 8,894,387 B2 | 11/2014 | White |
| 8,894,561 B2 | 11/2014 | Callaway et al. |
| 8,897,873 B2 | 11/2014 | Schima et al. |
| 8,900,060 B2 | 12/2014 | Liebing |
| 8,905,910 B2 | 12/2014 | Reichenbach et al. |
| 8,927,700 B2 | 1/2015 | McCauley et al. |
| 8,932,141 B2 | 1/2015 | Liebing |
| 8,932,197 B2 | 1/2015 | Gregoric et al. |
| 8,934,956 B2 | 1/2015 | Glenn et al. |
| 8,942,828 B1 | 1/2015 | Schecter |
| 8,944,748 B2 | 2/2015 | Liebing |
| 8,945,159 B2 | 2/2015 | Nussbaum |
| 8,956,402 B2 | 2/2015 | Cohn |
| 8,961,387 B2 | 2/2015 | Duncan |
| 8,961,466 B2 | 2/2015 | Steinbach |
| 8,971,980 B2 | 3/2015 | Mace et al. |
| 8,974,519 B2 | 3/2015 | Gennrich et al. |
| 8,992,406 B2 | 3/2015 | Corbett |
| 8,997,349 B2 | 4/2015 | Mori et al. |
| 9,002,468 B2 | 4/2015 | Shea et al. |
| 9,023,010 B2 | 5/2015 | Chiu et al. |
| 9,028,216 B2 | 5/2015 | Schumacher et al. |
| 9,028,392 B2 | 5/2015 | Shifflette |
| 9,028,859 B2 | 5/2015 | Hossainy et al. |
| 9,033,863 B2 | 5/2015 | Jarvik |
| 9,033,909 B2 | 5/2015 | Aihara |
| 9,039,595 B2 | 5/2015 | Ayre et al. |
| 9,044,236 B2 | 6/2015 | Nguyen et al. |
| 9,056,159 B2 | 6/2015 | Medvedev et al. |
| 9,066,992 B2 | 6/2015 | Stankus et al. |
| 9,067,005 B2 | 6/2015 | Ozaki et al. |
| 9,067,006 B2 | 6/2015 | Toellner |
| 9,072,825 B2 | 7/2015 | Pfeffer et al. |
| 9,078,692 B2 | 7/2015 | Shturman et al. |
| 9,089,329 B2 | 7/2015 | Hoarau et al. |
| 9,089,634 B2 | 7/2015 | Schumacher et al. |
| 9,089,635 B2 | 7/2015 | Reichenbach et al. |
| 9,089,670 B2 | 7/2015 | Scheckel |
| 9,095,428 B2 | 8/2015 | Kabir et al. |
| 9,096,703 B2 | 8/2015 | Li et al. |
| 9,101,302 B2 | 8/2015 | Mace et al. |
| 9,125,977 B2 | 9/2015 | Nishimura et al. |
| 9,127,680 B2 | 9/2015 | Yanal et al. |
| 9,138,516 B2 | 9/2015 | Vischer et al. |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,168,361 B2 | 10/2015 | Ehrenreich et al. |
| 9,180,227 B2 | 11/2015 | Ludwig et al. |
| 9,180,235 B2 | 11/2015 | Forsell |
| 9,192,705 B2 | 11/2015 | Yanai et al. |
| 9,199,020 B2 | 12/2015 | Siess |
| 9,217,442 B2 | 12/2015 | Wiessler et al. |
| D746,975 S | 1/2016 | Schenck et al. |
| 9,227,002 B1 | 1/2016 | Giridharan et al. |
| 9,239,049 B2 | 1/2016 | Jarnagin et al. |
| 9,265,870 B2 | 2/2016 | Reichenbach et al. |
| 9,278,189 B2 | 3/2016 | Corbett |
| 9,283,314 B2 | 3/2016 | Prasad et al. |
| 9,291,591 B2 | 3/2016 | Simmons et al. |
| 9,295,550 B2 | 3/2016 | Nguyen et al. |
| 9,295,767 B2 | 3/2016 | Schmid et al. |
| 9,308,302 B2 | 4/2016 | Zeng |
| 9,308,304 B2 | 4/2016 | Peters et al. |
| 9,314,558 B2 | 4/2016 | Er |
| 9,314,559 B2 | 4/2016 | Smith et al. |
| 9,328,741 B2 | 5/2016 | Liebing |
| 9,333,284 B2 | 5/2016 | Thompson et al. |
| 9,339,596 B2 | 5/2016 | Roehn |
| 9,345,824 B2 | 5/2016 | Mohl et al. |
| 9,358,329 B2 | 6/2016 | Fitzgerald et al. |
| 9,358,330 B2 | 6/2016 | Schumacher |
| 9,364,255 B2 | 6/2016 | Weber |
| 9,364,592 B2 | 6/2016 | McBride et al. |
| 9,370,613 B2 | 6/2016 | Hsu et al. |
| 9,375,445 B2 | 6/2016 | Hossainy et al. |
| 9,381,285 B2 | 7/2016 | Ozaki et al. |
| 9,387,284 B2 | 7/2016 | Heilman et al. |
| 9,409,012 B2 | 8/2016 | Eidenschink et al. |
| 9,416,783 B2 | 8/2016 | Schumacher et al. |
| 9,416,791 B2 | 8/2016 | Toellner |
| 9,421,311 B2 | 8/2016 | Tanner et al. |
| 9,433,713 B2 | 9/2016 | Corbett et al. |
| 9,435,450 B2 | 9/2016 | Muennich |
| 9,446,179 B2 | 9/2016 | Keenan et al. |
| 9,452,249 B2 | 9/2016 | Kearsley et al. |
| 9,474,840 B2 | 10/2016 | Siess |
| 9,486,565 B2 | 11/2016 | Göllner et al. |
| 9,492,601 B2 | 11/2016 | Casas et al. |
| 9,504,491 B2 | 11/2016 | Callas et al. |
| 9,511,179 B2 | 12/2016 | Casas et al. |
| 9,512,839 B2 | 12/2016 | Liebing |
| 9,522,257 B2 | 12/2016 | Webler |
| 9,526,818 B2 | 12/2016 | Kearsley et al. |
| 9,533,084 B2 | 1/2017 | Siess et al. |
| 9,533,085 B2 | 1/2017 | Hanna |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,555,177 B2 | 1/2017 | Curtis et al. |
| 9,556,873 B2 | 1/2017 | Yanal et al. |
| 9,561,309 B2 | 2/2017 | Glauser et al. |
| 9,561,313 B2 | 2/2017 | Taskin |
| 9,572,915 B2 * | 2/2017 | Heuring ............... A61M 60/33 |
| 9,592,328 B2 | 3/2017 | Jeevanandam et al. |
| 9,603,983 B2 | 3/2017 | Roehn et al. |
| 9,603,984 B2 | 3/2017 | Romero et al. |
| 9,611,743 B2 | 4/2017 | Toeliner et al. |
| 9,612,182 B2 | 4/2017 | Olde et al. |
| 9,616,157 B2 | 4/2017 | Akdis |
| 9,616,159 B2 | 4/2017 | Anderson et al. |
| 9,623,163 B1 | 4/2017 | Fischi |
| 9,631,754 B2 | 4/2017 | Richardson et al. |
| 9,642,984 B2 | 5/2017 | Schumacher et al. |
| 9,656,010 B2 | 5/2017 | Burke |
| 9,656,030 B1 | 5/2017 | Webler et al. |
| 9,662,211 B2 | 5/2017 | Hodson et al. |
| 9,669,141 B2 | 6/2017 | Parker et al. |
| 9,669,142 B2 | 6/2017 | Spanier et al. |
| 9,669,143 B2 | 6/2017 | Guerrero |
| 9,675,450 B2 | 6/2017 | Straka et al. |
| 9,675,738 B2 | 6/2017 | Tanner et al. |
| 9,675,739 B2 | 6/2017 | Tanner et al. |
| 9,675,742 B2 | 6/2017 | Casas et al. |
| 9,687,596 B2 | 6/2017 | Poirier |
| 9,687,630 B2 | 6/2017 | Basu et al. |
| 9,700,659 B2 | 7/2017 | Kantrowitz et al. |
| 9,713,662 B2 | 7/2017 | Rosenberg et al. |
| 9,713,663 B2 | 7/2017 | Medvedev et al. |
| 9,715,839 B2 | 7/2017 | Pybus et al. |
| 9,717,615 B2 | 8/2017 | Grandt |
| 9,717,832 B2 | 8/2017 | Taskin et al. |
| 9,717,839 B2 | 8/2017 | Hashimoto |
| 9,726,195 B2 | 8/2017 | Cecere et al. |
| 9,731,058 B2 | 8/2017 | Siebenhaar et al. |
| 9,731,101 B2 | 8/2017 | Bertrand et al. |
| 9,737,361 B2 | 8/2017 | Magana et al. |
| 9,737,651 B2 | 8/2017 | Wampler |
| 9,744,280 B2 | 8/2017 | Schade et al. |
| 9,744,287 B2 | 8/2017 | Bulent et al. |
| 9,750,859 B2 | 9/2017 | Bulent et al. |
| 9,757,502 B2 | 9/2017 | Burke et al. |
| 9,770,202 B2 | 9/2017 | Ralston et al. |
| 9,770,543 B2 | 9/2017 | Tanner et al. |
| 9,771,801 B2 | 9/2017 | Schumacher et al. |
| 9,775,930 B2 | 10/2017 | Michal et al. |
| 9,782,279 B2 | 10/2017 | Kassab |
| 9,782,527 B2 | 10/2017 | Thomas et al. |

(56) References Cited

U.S. PATENT DOCUMENTS

| | | |
|---|---|---|
| 9,795,780 B2 | 10/2017 | Serna et al. |
| 9,801,987 B2 | 10/2017 | Faman et al. |
| 9,801,992 B2 | 10/2017 | Giordano et al. |
| 9,821,098 B2 | 11/2017 | Horvath et al. |
| 9,821,146 B2 | 11/2017 | Tao et al. |
| 9,827,356 B2 | 11/2017 | Muller et al. |
| 9,833,314 B2 | 12/2017 | Corbett |
| 9,833,550 B2 | 12/2017 | Siess |
| 9,833,551 B2 | 12/2017 | Criscione et al. |
| 9,839,734 B1 | 12/2017 | Menon et al. |
| 9,844,618 B2 | 12/2017 | Muller-Spanka et al. |
| 9,850,906 B2 | 12/2017 | Ozaki et al. |
| 9,855,437 B2 | 1/2018 | Nguyen et al. |
| 9,861,504 B2 | 1/2018 | Abunassar et al. |
| 9,861,731 B2 | 1/2018 | Tamburino |
| 9,872,948 B2 | 1/2018 | Siess |
| 9,878,087 B2 | 1/2018 | Richardson et al. |
| 9,878,169 B2 | 1/2018 | Hossainy |
| 9,889,242 B2 | 2/2018 | Pfeffer et al. |
| 9,895,244 B2 | 2/2018 | Papp et al. |
| 9,895,475 B2 | 2/2018 | Toellner et al. |
| 9,907,890 B2 | 3/2018 | Muller |
| 9,907,892 B2 | 3/2018 | Broen et al. |
| 9,913,937 B2 | 3/2018 | Schwammenthal et al. |
| 9,918,822 B2 | 3/2018 | Abunassar et al. |
| 9,919,085 B2 | 3/2018 | Throckmorton et al. |
| 9,919,088 B2 | 3/2018 | Bonde et al. |
| 9,919,089 B2 | 3/2018 | Garrigue |
| 9,950,101 B2 | 4/2018 | Smith et al. |
| 9,956,410 B2 | 5/2018 | Deem et al. |
| 9,962,258 B2 | 5/2018 | Seguin et al. |
| 9,974,893 B2 | 5/2018 | Toellner |
| 9,974,894 B2 | 5/2018 | Morello |
| 9,981,078 B2 | 5/2018 | Jin et al. |
| 9,985,374 B2 | 5/2018 | Hodges |
| 9,987,407 B2 | 6/2018 | Grant et al. |
| 10,010,273 B2 | 7/2018 | Sloan et al. |
| 10,022,499 B2 | 7/2018 | Galasso |
| 10,028,835 B2 | 7/2018 | Kermode et al. |
| 10,029,037 B2 | 7/2018 | Muller et al. |
| 10,029,038 B2 | 7/2018 | Hodges |
| 10,029,039 B2 | 7/2018 | Dague et al. |
| 10,031,124 B2 | 7/2018 | Galasso |
| 10,034,972 B2 | 7/2018 | Wampler et al. |
| 10,039,873 B2 | 8/2018 | Siegenthaler |
| 10,046,146 B2 | 8/2018 | Manderfeld et al. |
| 10,052,419 B2 | 8/2018 | Er |
| 10,058,349 B2 | 8/2018 | Gunderson et al. |
| 10,058,641 B2 | 8/2018 | Mollison et al. |
| 10,058,652 B2 | 8/2018 | Tsoukalis |
| 10,058,653 B2 | 8/2018 | Wang et al. |
| 10,077,777 B2 | 9/2018 | Horvath et al. |
| 10,080,828 B2 | 9/2018 | Wiesener et al. |
| 10,080,834 B2 | 9/2018 | Federspiel et al. |
| 10,080,871 B2 | 9/2018 | Schumacher et al. |
| 10,208,763 B2 | 2/2019 | Schumacher et al. |
| 10,357,598 B2 | 7/2019 | Aboul-Hosn et al. |
| 10,569,005 B2 | 2/2020 | Solem et al. |
| 10,722,631 B2 | 7/2020 | Salahieh et al. |
| 10,881,770 B2 | 1/2021 | Tuval et al. |
| 10,894,115 B2 | 1/2021 | Pfeffer et al. |
| 11,033,727 B2 * | 6/2021 | Tuval ................ A61M 60/416 |
| 11,123,538 B2 | 9/2021 | Epple et al. |
| 11,185,677 B2 | 11/2021 | Salahieh et al. |
| 11,229,784 B2 | 1/2022 | Salahieh et al. |
| 11,268,521 B2 | 3/2022 | Toellner |
| 11,280,345 B2 | 3/2022 | Bredenbreuker et al. |
| 11,850,413 B2 | 12/2023 | Zeng et al. |
| 12,017,056 B2 | 6/2024 | Guo et al. |
| 2001/0003802 A1 | 6/2001 | Vitale |
| 2001/0023369 A1 | 9/2001 | Chobotov |
| 2001/0046380 A1 | 11/2001 | LeFebvre |
| 2001/0053928 A1 | 12/2001 | Edelman et al. |
| 2002/0057989 A1 | 5/2002 | Afzal et al. |
| 2002/0058971 A1 | 5/2002 | Zarinetchi et al. |
| 2002/0068848 A1 | 6/2002 | Zadini et al. |
| 2002/0072679 A1 | 6/2002 | Schock et al. |
| 2002/0072779 A1 | 6/2002 | Loeb |
| 2002/0128709 A1 | 9/2002 | Pless |
| 2002/0147495 A1 | 10/2002 | Petroff |
| 2003/0069465 A1 | 4/2003 | Benkowski et al. |
| 2003/0088151 A1 | 5/2003 | Kung et al. |
| 2003/0131995 A1 | 7/2003 | de Rouffignac et al. |
| 2003/0155111 A1 | 8/2003 | Vinegar et al. |
| 2003/0173081 A1 | 9/2003 | Vinegar et al. |
| 2003/0173082 A1 | 9/2003 | Vinegar et al. |
| 2003/0173085 A1 | 9/2003 | Vinegar et al. |
| 2003/0178191 A1 | 9/2003 | Maher et al. |
| 2003/0209348 A1 | 11/2003 | Ward et al. |
| 2003/0217957 A1 | 11/2003 | Bowman et al. |
| 2004/0024285 A1 | 2/2004 | Muckter |
| 2004/0040715 A1 | 3/2004 | Wellington et al. |
| 2004/0097782 A1 | 5/2004 | Korakianitis et al. |
| 2004/0097783 A1 | 5/2004 | Peters et al. |
| 2004/0228724 A1 | 11/2004 | Capone et al. |
| 2004/0249363 A1 | 12/2004 | Burke et al. |
| 2005/0010077 A1 | 1/2005 | Calderon |
| 2005/0043805 A1 | 2/2005 | Chudik |
| 2005/0049696 A1 | 3/2005 | Siess et al. |
| 2005/0060036 A1 | 3/2005 | Schultz et al. |
| 2005/0113632 A1 | 5/2005 | Ortiz et al. |
| 2005/0119599 A1 | 6/2005 | Kanz et al. |
| 2005/0187616 A1 | 8/2005 | Realyvasquez |
| 2005/0209617 A1 | 9/2005 | Koven et al. |
| 2005/0220636 A1 | 10/2005 | Henein et al. |
| 2005/0246010 A1 | 11/2005 | Alexander et al. |
| 2005/0254976 A1 | 11/2005 | Carrier et al. |
| 2005/0256540 A1 | 11/2005 | Silver et al. |
| 2005/0277803 A1 | 12/2005 | Pecor |
| 2006/0111641 A1 | 5/2006 | Manera et al. |
| 2006/0116700 A1 | 6/2006 | Crow |
| 2006/0129082 A1 | 6/2006 | Rozga |
| 2006/0155158 A1 | 7/2006 | Hosn |
| 2006/0177343 A1 | 8/2006 | Brian et al. |
| 2006/0195098 A1 | 8/2006 | Schumacher |
| 2006/0257355 A1 | 11/2006 | Stewart et al. |
| 2006/0293664 A1 | 12/2006 | Schumacher |
| 2007/0106274 A1 | 5/2007 | Ayre et al. |
| 2007/0167091 A1 | 7/2007 | Schumacher |
| 2007/0203453 A1 | 8/2007 | Mori et al. |
| 2007/0213690 A1 | 9/2007 | Phillips et al. |
| 2007/0250148 A1 | 10/2007 | Perry et al. |
| 2007/0253842 A1 | 11/2007 | Horvath et al. |
| 2007/0265673 A1 | 11/2007 | Ransbury et al. |
| 2007/0270633 A1 | 11/2007 | Cook et al. |
| 2007/0299314 A1 | 12/2007 | Bertolero et al. |
| 2008/0045779 A1 | 2/2008 | Rinaldi et al. |
| 2008/0065014 A1 | 3/2008 | Von Oepen et al. |
| 2008/0076101 A1 | 3/2008 | Hyde et al. |
| 2008/0097273 A1 | 4/2008 | Levin et al. |
| 2008/0097562 A1 | 4/2008 | Tan |
| 2008/0119421 A1 | 5/2008 | Tuszynski et al. |
| 2008/0132748 A1 | 6/2008 | Shifflette |
| 2008/0132749 A1 | 6/2008 | Hegde et al. |
| 2008/0167679 A1 | 7/2008 | Papp |
| 2008/0167711 A1 | 7/2008 | Roorda |
| 2008/0188923 A1 | 8/2008 | Chu |
| 2008/0200750 A1 | 8/2008 | James |
| 2008/0208329 A1 | 8/2008 | Bishop et al. |
| 2008/0228026 A1 | 9/2008 | Manera et al. |
| 2008/0240947 A1 | 10/2008 | Allaire et al. |
| 2008/0243030 A1 | 10/2008 | Seibel et al. |
| 2008/0275295 A1 | 11/2008 | Gertner |
| 2008/0275354 A1 | 11/2008 | Thuramalla et al. |
| 2008/0296433 A1 | 12/2008 | Brenner et al. |
| 2008/0300677 A1 | 12/2008 | Schrayer |
| 2009/0012460 A1 | 1/2009 | Steck et al. |
| 2009/0061072 A1 | 3/2009 | Isch et al. |
| 2009/0063402 A1 | 3/2009 | Hayter |
| 2009/0082723 A1 | 3/2009 | Krogh et al. |
| 2009/0143635 A1 | 6/2009 | Benkowski et al. |
| 2009/0171448 A1 | 7/2009 | Eli |
| 2009/0177028 A1 | 7/2009 | White |
| 2009/0182307 A1 | 7/2009 | Yap et al. |

(56) References Cited

U.S. PATENT DOCUMENTS

| | | |
|---|---|---|
| 2009/0188964 A1 | 7/2009 | Orlov |
| 2009/0259089 A1 | 10/2009 | Gelbart et al. |
| 2010/0016703 A1 | 1/2010 | Batkin et al. |
| 2010/0022943 A1 | 1/2010 | Mauch et al. |
| 2010/0042037 A1 | 2/2010 | Felt et al. |
| 2010/0076380 A1 | 3/2010 | Hui |
| 2010/0084326 A1 | 4/2010 | Takesawa |
| 2010/0087742 A1 | 4/2010 | Bishop et al. |
| 2010/0105978 A1 | 4/2010 | Matsui et al. |
| 2010/0152523 A1 | 6/2010 | MacDonald et al. |
| 2010/0152525 A1 | 6/2010 | Weizman et al. |
| 2010/0152526 A1 | 6/2010 | Pacella et al. |
| 2010/0160751 A1 | 6/2010 | Hete et al. |
| 2010/0184318 A1 | 7/2010 | Bogart et al. |
| 2010/0185220 A1 | 7/2010 | Naghavi et al. |
| 2010/0222635 A1 | 9/2010 | Poirier |
| 2010/0222878 A1 | 9/2010 | Poirier |
| 2010/0249489 A1 | 9/2010 | Jarvik |
| 2011/0098548 A1 | 4/2011 | Budiman et al. |
| 2011/0106115 A1 | 5/2011 | Haselby et al. |
| 2011/0106120 A1 | 5/2011 | Haselby et al. |
| 2011/0178596 A1 | 7/2011 | Hauck et al. |
| 2011/0224655 A1 | 9/2011 | Asirvatham et al. |
| 2011/0297599 A1 | 12/2011 | Lo et al. |
| 2011/0301625 A1 | 12/2011 | Mauch et al. |
| 2011/0304240 A1 | 12/2011 | Meitav et al. |
| 2012/0022316 A1 | 1/2012 | Aboul-Hosn et al. |
| 2012/0028908 A1 | 2/2012 | Viswanath et al. |
| 2012/0039711 A1 | 2/2012 | Roehn |
| 2012/0109060 A1 | 5/2012 | Kick et al. |
| 2012/0165641 A1 | 6/2012 | Burnett et al. |
| 2012/0179184 A1 | 7/2012 | Orlov |
| 2012/0184803 A1 | 7/2012 | Simon et al. |
| 2012/0190918 A1 | 7/2012 | Oepen et al. |
| 2012/0239139 A1 | 9/2012 | Wnendt et al. |
| 2012/0252709 A1 | 10/2012 | Felts et al. |
| 2012/0289928 A1 | 11/2012 | Wright et al. |
| 2012/0302458 A1 | 11/2012 | Adamczyk et al. |
| 2012/0330683 A1 | 12/2012 | Ledwidge et al. |
| 2013/0023373 A1 | 1/2013 | Janek |
| 2013/0040407 A1 | 2/2013 | Brophy et al. |
| 2013/0053693 A1 | 2/2013 | Breznock et al. |
| 2013/0144144 A1 | 6/2013 | Laster et al. |
| 2013/0211489 A1 | 8/2013 | Makower et al. |
| 2013/0233798 A1 | 9/2013 | Wiktor et al. |
| 2013/0245360 A1 | 9/2013 | Schumacher |
| 2013/0267892 A1 | 10/2013 | Woolford |
| 2013/0281761 A1 | 10/2013 | Kapur |
| 2013/0289696 A1 | 10/2013 | Maggard et al. |
| 2013/0310845 A1 | 11/2013 | Thor et al. |
| 2013/0317604 A1 | 11/2013 | Min et al. |
| 2013/0344047 A1 | 12/2013 | Pacetti et al. |
| 2014/0017200 A1 | 1/2014 | Michal et al. |
| 2014/0039465 A1 | 2/2014 | Schulz et al. |
| 2014/0039603 A1 | 2/2014 | Wang |
| 2014/0051908 A1 | 2/2014 | Khanal et al. |
| 2014/0058190 A1 | 2/2014 | Gohean et al. |
| 2014/0066693 A1 | 3/2014 | Goldfarb et al. |
| 2014/0128659 A1* | 5/2014 | Heuring .............. A61M 60/237 600/16 |
| 2014/0128795 A1 | 5/2014 | Keren et al. |
| 2014/0142617 A1 | 5/2014 | Larsen et al. |
| 2014/0148638 A1 | 5/2014 | LaRose et al. |
| 2014/0163664 A1 | 6/2014 | Goldsmith |
| 2014/0190523 A1 | 7/2014 | Garvey et al. |
| 2014/0194678 A1 | 7/2014 | Wildhirt et al. |
| 2014/0194717 A1 | 7/2014 | Wildhirt et al. |
| 2014/0199377 A1 | 7/2014 | Stankus et al. |
| 2014/0200655 A1 | 7/2014 | Webler et al. |
| 2014/0207232 A1 | 7/2014 | Garrigue |
| 2014/0228741 A1 | 8/2014 | Frankowski et al. |
| 2014/0243970 A1 | 8/2014 | Yanai |
| 2014/0255176 A1 | 9/2014 | Bredenbreuker et al. |
| 2014/0260551 A1 | 9/2014 | Gray et al. |
| 2014/0275721 A1 | 9/2014 | Yanai et al. |
| 2014/0275725 A1 | 9/2014 | Schenck et al. |
| 2014/0288354 A1 | 9/2014 | Timms et al. |
| 2014/0309481 A1 | 10/2014 | Medvedev et al. |
| 2014/0336444 A1 | 11/2014 | Bonde |
| 2014/0336486 A1 | 11/2014 | Ouyang et al. |
| 2014/0336747 A1 | 11/2014 | Rapoza et al. |
| 2014/0341726 A1 | 11/2014 | Wu et al. |
| 2014/0350328 A1 | 11/2014 | Mohl |
| 2014/0357938 A1 | 12/2014 | Pilla et al. |
| 2014/0370073 A1 | 12/2014 | Tang et al. |
| 2015/0005571 A1 | 1/2015 | Jeffery et al. |
| 2015/0018747 A1 | 1/2015 | Michal et al. |
| 2015/0031938 A1 | 1/2015 | Crosby et al. |
| 2015/0051437 A1 | 2/2015 | Miyakoshi et al. |
| 2015/0068069 A1 | 3/2015 | Tran et al. |
| 2015/0080639 A1 | 3/2015 | Radziemski et al. |
| 2015/0080743 A1 | 3/2015 | Siess |
| 2015/0087890 A1 | 3/2015 | Spanier et al. |
| 2015/0101645 A1 | 4/2015 | Neville et al. |
| 2015/0112210 A1 | 4/2015 | Webler |
| 2015/0119859 A1 | 4/2015 | Cajamarca et al. |
| 2015/0120323 A1 | 4/2015 | Galasso et al. |
| 2015/0134048 A1 | 5/2015 | Ding |
| 2015/0152878 A1 | 6/2015 | McBride et al. |
| 2015/0159643 A1 | 6/2015 | Koob |
| 2015/0174060 A1 | 6/2015 | Heit et al. |
| 2015/0191607 A1 | 7/2015 | McDaniel |
| 2015/0207331 A1 | 7/2015 | Petersen |
| 2015/0216685 A1 | 8/2015 | Spence et al. |
| 2015/0222128 A1 | 8/2015 | Hansen |
| 2015/0222139 A1 | 8/2015 | Petersen et al. |
| 2015/0226691 A1 | 8/2015 | Wang et al. |
| 2015/0230709 A1 | 8/2015 | Milner et al. |
| 2015/0231317 A1 | 8/2015 | Schima et al. |
| 2015/0238671 A1 | 8/2015 | Mesallum |
| 2015/0265757 A1 | 9/2015 | Dowling et al. |
| 2015/0283027 A1 | 10/2015 | Lampe et al. |
| 2015/0285258 A1 | 10/2015 | Foster |
| 2015/0290370 A1 | 10/2015 | Crunkleton et al. |
| 2015/0290377 A1 | 10/2015 | Kearsley et al. |
| 2015/0306291 A1 | 10/2015 | Bonde et al. |
| 2015/0320926 A1 | 11/2015 | Fitzpatrick et al. |
| 2015/0328382 A1 | 11/2015 | Corbett et al. |
| 2015/0335803 A1 | 11/2015 | Yamane |
| 2015/0364861 A1 | 12/2015 | Lucke et al. |
| 2015/0366495 A1 | 12/2015 | Gable, III et al. |
| 2015/0367050 A1 | 12/2015 | Bulent et al. |
| 2015/0368335 A1 | 12/2015 | Banerjee et al. |
| 2015/0374892 A1 | 12/2015 | Yanai et al. |
| 2016/0022887 A1 | 1/2016 | Wampler |
| 2016/0022890 A1 | 1/2016 | Schwammenthal et al. |
| 2016/0030649 A1 | 2/2016 | Zeng |
| 2016/0038315 A1 | 2/2016 | Consigny et al. |
| 2016/0045098 A1 | 2/2016 | Tsubouchi |
| 2016/0045652 A1 | 2/2016 | Cornen |
| 2016/0045654 A1 | 2/2016 | Connor |
| 2016/0053763 A1 | 2/2016 | Toellner |
| 2016/0058434 A1 | 3/2016 | Delaloye et al. |
| 2016/0067395 A1 | 3/2016 | Jimenez et al. |
| 2016/0085714 A1 | 3/2016 | Goodnow et al. |
| 2016/0175044 A1 | 6/2016 | Abunassar et al. |
| 2016/0182158 A1 | 6/2016 | Lee et al. |
| 2016/0184499 A1 | 6/2016 | Ricci et al. |
| 2016/0199543 A1 | 7/2016 | Venkateswara-Rao |
| 2016/0199556 A1 | 7/2016 | Ayre et al. |
| 2016/0199557 A1 | 7/2016 | Bluvshtein et al. |
| 2016/0203275 A1 | 7/2016 | Benjamin et al. |
| 2016/0206798 A1 | 7/2016 | Williams et al. |
| 2016/0220269 A1 | 8/2016 | Labropoulos et al. |
| 2016/0220785 A1 | 8/2016 | Fabro |
| 2016/0222969 A1 | 8/2016 | Heide et al. |
| 2016/0250399 A1 | 9/2016 | Tiller et al. |
| 2016/0250400 A1 | 9/2016 | Schumacher |
| 2016/0251720 A1 | 9/2016 | Schulze et al. |
| 2016/0256620 A1 | 9/2016 | Scheckel et al. |
| 2016/0263299 A1 | 9/2016 | Xu et al. |
| 2016/0271161 A1 | 9/2016 | Dobson |
| 2016/0271309 A1 | 9/2016 | Throckmorton et al. |
| 2016/0279310 A1 | 9/2016 | Scheckel et al. |

(56) References Cited

U.S. PATENT DOCUMENTS

| | | |
|---|---|---|
| 2016/0303301 A1 | 10/2016 | Bluvshtein et al. |
| 2016/0308403 A1 | 10/2016 | Bluvshtein et al. |
| 2016/0317291 A1 | 11/2016 | Bishop et al. |
| 2016/0317333 A1 | 11/2016 | Ainsworth et al. |
| 2016/0325034 A1 | 11/2016 | Wiktor et al. |
| 2016/0348688 A1 | 12/2016 | Schumacher et al. |
| 2016/0354526 A1 | 12/2016 | Whisenant et al. |
| 2016/0375187 A1 | 12/2016 | Lee et al. |
| 2017/0000361 A1 | 1/2017 | Meyering et al. |
| 2017/0000935 A1 | 1/2017 | Vasilyev et al. |
| 2017/0007552 A1 | 1/2017 | Slepian |
| 2017/0007762 A1 | 1/2017 | Hayter et al. |
| 2017/0014401 A1 | 1/2017 | Dalton et al. |
| 2017/0014562 A1 | 1/2017 | Liebing |
| 2017/0021074 A1 | 1/2017 | Opfermann et al. |
| 2017/0028114 A1 | 2/2017 | Göllner et al. |
| 2017/0028115 A1 | 2/2017 | Muller |
| 2017/0035952 A1 | 2/2017 | Muller |
| 2017/0035954 A1 | 2/2017 | Muller et al. |
| 2017/0037860 A1 | 2/2017 | Toellner |
| 2017/0043076 A1 | 2/2017 | Wampler et al. |
| 2017/0063143 A1 | 3/2017 | Hoarau et al. |
| 2017/0080136 A1 | 3/2017 | Janeczek et al. |
| 2017/0100527 A1 | 4/2017 | Schwammenthal et al. |
| 2017/0112984 A1 | 4/2017 | Vargas Fonseca |
| 2017/0119945 A1 | 5/2017 | Neumann |
| 2017/0119946 A1 | 5/2017 | McChrystal et al. |
| 2017/0136165 A1 | 5/2017 | Hansen et al. |
| 2017/0136225 A1 | 5/2017 | Siess et al. |
| 2017/0143883 A1 | 5/2017 | Spence |
| 2017/0143952 A1 | 5/2017 | Siess et al. |
| 2017/0157309 A1 | 6/2017 | Begg et al. |
| 2017/0173242 A1 | 6/2017 | Anderson et al. |
| 2017/0193184 A1 | 7/2017 | Hayter et al. |
| 2017/0196638 A1 | 7/2017 | Semna et al. |
| 2017/0202575 A1 | 7/2017 | Stanfield et al. |
| 2017/0215918 A1 | 8/2017 | Tao et al. |
| 2017/0224896 A1 | 8/2017 | Graham et al. |
| 2017/0232168 A1 | 8/2017 | Reichenbach et al. |
| 2017/0232169 A1 | 8/2017 | Muller |
| 2017/0232172 A1 | 8/2017 | Mesallum |
| 2017/0239407 A1 | 8/2017 | Hayward |
| 2017/0250575 A1 | 8/2017 | Wong et al. |
| 2017/0265994 A1 | 9/2017 | Krone |
| 2017/0274128 A1 | 9/2017 | Tamburino et al. |
| 2017/0281025 A9 | 10/2017 | Glover et al. |
| 2017/0281841 A1 | 10/2017 | Larose et al. |
| 2017/0281842 A1 | 10/2017 | Larose et al. |
| 2017/0290964 A1 | 10/2017 | Barry |
| 2017/0296227 A1 | 10/2017 | Osypka |
| 2017/0296725 A1 | 10/2017 | Peters et al. |
| 2017/0312106 A1 | 11/2017 | Gomez et al. |
| 2017/0312416 A1 | 11/2017 | Strueber |
| 2017/0312492 A1 | 11/2017 | Fantuzzi et al. |
| 2017/0319113 A1 | 11/2017 | Hurd et al. |
| 2017/0323713 A1 | 11/2017 | Moeller et al. |
| 2017/0325943 A1 | 11/2017 | Robin et al. |
| 2017/0333607 A1 | 11/2017 | Zarins |
| 2017/0333673 A1 | 11/2017 | Tuval et al. |
| 2017/0340788 A1 | 11/2017 | Korakianitis et al. |
| 2017/0340789 A1 | 11/2017 | Bonde et al. |
| 2017/0340790 A1 | 11/2017 | Wiesener et al. |
| 2017/0348470 A1 | 12/2017 | D'Ambrosio et al. |
| 2017/0360309 A1 | 12/2017 | Moore et al. |
| 2017/0361001 A1 | 12/2017 | Canatella et al. |
| 2017/0361011 A1 | 12/2017 | Muennich et al. |
| 2017/0363103 A1 | 12/2017 | Canatella et al. |
| 2017/0363210 A1 | 12/2017 | Durst et al. |
| 2017/0363620 A1 | 12/2017 | Beshiri et al. |
| 2017/0368246 A1 | 12/2017 | Criscione et al. |
| 2017/0370365 A1 | 12/2017 | Fritz et al. |
| 2018/0001003 A1 | 1/2018 | Moran et al. |
| 2018/0001007 A1 | 1/2018 | Stratton |
| 2018/0001012 A1 | 1/2018 | Ardehali |
| 2018/0001062 A1 | 1/2018 | O'Carrol et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0021497 A1 | 1/2018 | Nunez et al. |
| 2018/0028736 A1 | 2/2018 | Wong et al. |
| 2018/0035926 A1 | 2/2018 | Stafford |
| 2018/0040418 A1 | 2/2018 | Hansen et al. |
| 2018/0047282 A1 | 2/2018 | He et al. |
| 2018/0050139 A1 | 2/2018 | Siess et al. |
| 2018/0050140 A1 | 2/2018 | Siess et al. |
| 2018/0050142 A1 | 2/2018 | Siess et al. |
| 2018/0055383 A1 | 3/2018 | Manera |
| 2018/0055983 A1 | 3/2018 | Bourque |
| 2018/0058437 A1 | 3/2018 | Ellers et al. |
| 2018/0064862 A1 | 3/2018 | Keenan et al. |
| 2018/0071020 A1 | 3/2018 | Laufer et al. |
| 2018/0078159 A1 | 3/2018 | Edelman et al. |
| 2018/0080326 A1 | 3/2018 | Schumacher et al. |
| 2018/0085505 A1 | 3/2018 | Casas |
| 2018/0085507 A1 | 3/2018 | Casas et al. |
| 2018/0085509 A1 | 3/2018 | Petersen |
| 2018/0093026 A1 | 4/2018 | Angwin et al. |
| 2018/0097368 A1 | 4/2018 | Hansen |
| 2018/0099076 A1 | 4/2018 | Larose |
| 2018/0099078 A1 | 4/2018 | Tuseth et al. |
| 2018/0100507 A1 | 4/2018 | Wu et al. |
| 2018/0103611 A1 | 4/2018 | Mainini et al. |
| 2018/0103870 A1 | 4/2018 | Limaye et al. |
| 2018/0108275 A1 | 4/2018 | Newberry et al. |
| 2018/0110514 A1 | 4/2018 | Hoarau et al. |
| 2018/0114426 A1 | 4/2018 | Lee |
| 2018/0133380 A1 | 5/2018 | Liebing |
| 2018/0140759 A1 | 5/2018 | Kaiser et al. |
| 2018/0140801 A1 | 5/2018 | Voss et al. |
| 2018/0146968 A1 | 5/2018 | Nitzan et al. |
| 2018/0149164 A1 | 5/2018 | Siess |
| 2018/0149165 A1 | 5/2018 | Siess et al. |
| 2018/0154051 A1 | 6/2018 | Hossainy et al. |
| 2018/0154128 A1 | 6/2018 | Woo et al. |
| 2018/0161540 A1 | 6/2018 | Fantuzzi et al. |
| 2018/0161555 A1 | 6/2018 | Zhadkevich |
| 2018/0168469 A1 | 6/2018 | Granegger |
| 2018/0169312 A1 | 6/2018 | Barry |
| 2018/0169313 A1 | 6/2018 | Schwammenthal et al. |
| 2018/0193543 A1 | 7/2018 | Sun |
| 2018/0193614 A1 | 7/2018 | Nitzan et al. |
| 2018/0193616 A1 | 7/2018 | Nitzan et al. |
| 2018/0200420 A1 | 7/2018 | Di Paola et al. |
| 2018/0200422 A1 | 7/2018 | Nguyen et al. |
| 2018/0202962 A1 | 7/2018 | Simmons et al. |
| 2018/0207334 A1 | 7/2018 | Siess |
| 2018/0207337 A1 | 7/2018 | Spence et al. |
| 2018/0207338 A1 | 7/2018 | Bluvshtein et al. |
| 2018/0226997 A1 | 8/2018 | Jia |
| 2018/0228953 A1 | 8/2018 | Siess et al. |
| 2018/0228957 A1 | 8/2018 | Colella |
| 2018/0242891 A1 | 8/2018 | Bernstein et al. |
| 2018/0242976 A1 | 8/2018 | Kizuka |
| 2018/0243086 A1 | 8/2018 | Barbarino et al. |
| 2018/0243488 A1 | 8/2018 | Callaway et al. |
| 2018/0243489 A1 | 8/2018 | Haddadi |
| 2018/0243490 A1 | 8/2018 | Kallenbach et al. |
| 2018/0243492 A1 | 8/2018 | Salys |
| 2018/0250457 A1 | 9/2018 | Morello et al. |
| 2018/0250458 A1 | 9/2018 | Petersen et al. |
| 2018/0256242 A1 | 9/2018 | Bluvshtein et al. |
| 2018/0256794 A1 | 9/2018 | Rodefeld |
| 2018/0256795 A1 | 9/2018 | Schade et al. |
| 2018/0256797 A1 | 9/2018 | Schenck et al. |
| 2018/0256798 A1 | 9/2018 | Botterbusch et al. |
| 2018/0256859 A1 | 9/2018 | Korkuch |
| 2018/0264183 A1 | 9/2018 | Jahangir |
| 2018/0264184 A1 | 9/2018 | Jeffries et al. |
| 2018/0269692 A1 | 9/2018 | Petersen et al. |
| 2018/0280598 A1 | 10/2018 | Curran et al. |
| 2018/0280599 A1 | 10/2018 | Harjes et al. |
| 2018/0280600 A1 | 10/2018 | Harjes et al. |
| 2018/0280601 A1 | 10/2018 | Harjes et al. |
| 2018/0280604 A1 | 10/2018 | Hobro et al. |

(56) References Cited

U.S. PATENT DOCUMENTS

| | | | |
|---|---|---|---|
| 2018/0289295 A1 | 10/2018 | Hoss et al. | |
| 2018/0289876 A1 | 10/2018 | Nguyen et al. | |
| 2018/0289877 A1 | 10/2018 | Schumacher et al. | |
| 2018/0296572 A1 | 10/2018 | Deisher | |
| 2018/0303990 A1 | 10/2018 | Siess et al. | |
| 2019/0030231 A1 | 1/2019 | Aboul-Hosn et al. | |
| 2019/0070345 A1 | 3/2019 | McBride et al. | |
| 2019/0076167 A1 | 3/2019 | Fantuzzi et al. | |
| 2019/0083690 A1 | 3/2019 | Siess et al. | |
| 2019/0143018 A1 | 5/2019 | Salahich et al. | |
| 2019/0167873 A1 | 6/2019 | Koike et al. | |
| 2019/0209751 A1 | 7/2019 | Tuval et al. | |
| 2019/0269840 A1* | 9/2019 | Tuval | A61M 60/416 |
| 2019/0290822 A1 | 9/2019 | Igarashi | |
| 2019/0321531 A1 | 10/2019 | Cambronne et al. | |
| 2020/0029951 A1 | 1/2020 | Bessler et al. | |
| 2020/0030510 A1 | 1/2020 | Higgins | |
| 2020/0038568 A1 | 2/2020 | Higgins et al. | |
| 2020/0121835 A1 | 4/2020 | Farago et al. | |
| 2020/0237981 A1 | 7/2020 | Tuval et al. | |
| 2020/0246527 A1 | 8/2020 | Hildebrand et al. | |
| 2020/0316268 A1 | 10/2020 | Antoni et al. | |
| 2020/0391014 A1 | 12/2020 | Walters et al. | |
| 2021/0008261 A1 | 1/2021 | Calomeni et al. | |
| 2021/0023285 A1 | 1/2021 | Brandt | |
| 2021/0038786 A1 | 2/2021 | Calomeni et al. | |
| 2021/0052794 A1 | 2/2021 | Tuval et al. | |
| 2021/0113212 A1 | 4/2021 | Lashinski et al. | |
| 2021/0121679 A1 | 4/2021 | Mohl et al. | |
| 2021/0138201 A1 | 5/2021 | Schumacher et al. | |
| 2021/0236797 A1 | 8/2021 | D'Ambrosio et al. | |
| 2021/0244937 A1 | 8/2021 | Calomeni et al. | |
| 2021/0252271 A1 | 8/2021 | Wallin et al. | |
| 2021/0252274 A1 | 8/2021 | Dhaliwal et al. | |
| 2021/0308444 A1 | 10/2021 | Saul et al. | |
| 2022/0080178 A1 | 3/2022 | Salahieh et al. | |
| 2022/0105337 A1 | 4/2022 | Salahieh et al. | |
| 2022/0203084 A1 | 6/2022 | Zarins et al. | |
| 2022/0233841 A1 | 7/2022 | Hildebrand et al. | |
| 2022/0273933 A1 | 9/2022 | Ryan et al. | |
| 2023/0218886 A1 | 7/2023 | Robinson et al. | |
| 2023/0264012 A1 | 8/2023 | Brandt | |
| 2023/0390544 A1 | 12/2023 | Hildebrand et al. | |
| 2023/0405298 A1 | 12/2023 | Hildebrand et al. | |
| 2023/0414920 A1 | 12/2023 | Salahleh et al. | |
| 2024/0001101 A1 | 1/2024 | Wallin et al. | |
| 2024/0115849 A1 | 4/2024 | Dhaliwal et al. | |
| 2024/0139499 A1 | 5/2024 | Salahleh et al. | |
| 2024/0149046 A1 | 5/2024 | Calomeni et al. | |
| 2024/0157117 A1 | 5/2024 | Ryan et al. | |
| 2024/0173540 A1 | 5/2024 | Wallin et al. | |
| 2024/0181238 A1 | 6/2024 | Ryan et al. | |

FOREIGN PATENT DOCUMENTS

| | | |
|---|---|---|
| CA | 3014105 A1 | 8/2017 |
| CN | 1040073 A | 2/1990 |
| CN | 1008307 B | 6/1990 |
| CN | 1053108 A | 7/1991 |
| CN | 1105103 A | 7/1995 |
| CN | 1146329 A | 4/1997 |
| CN | 1179708 A | 4/1998 |
| CN | 2326258 Y | 6/1999 |
| CN | 1222862 A | 7/1999 |
| CN | 1045058 C | 9/1999 |
| CN | 1235849 A | 11/1999 |
| CN | 2361290 Y | 2/2000 |
| CN | 1254598 A | 5/2000 |
| CN | 2386827 Y | 7/2000 |
| CN | 2412579 Y | 1/2001 |
| CN | 2417173 Y | 1/2001 |
| CN | 1310647 A | 8/2001 |
| CN | 1342497 A | 4/2002 |
| CN | 1088795 C | 8/2002 |
| CN | 2504815 Y | 8/2002 |
| CN | 1376523 A | 10/2002 |
| CN | 1097138 C | 12/2002 |
| CN | 1105581 C | 4/2003 |
| CN | 1421248 A | 6/2003 |
| CN | 2558386 Y | 7/2003 |
| CN | 1118304 C | 8/2003 |
| CN | 1436048 A | 8/2003 |
| CN | 1120729 C | 9/2003 |
| CN | 2574609 Y | 9/2003 |
| CN | 1140228 C | 3/2004 |
| CN | 1161581 C | 8/2004 |
| CN | 1167472 C | 9/2004 |
| CN | 1527906 A | 9/2004 |
| CN | 1559361 A | 1/2005 |
| CN | 1559626 A | 1/2005 |
| CN | 1572331 A | 2/2005 |
| CN | 1202871 C | 5/2005 |
| CN | 1679974 A | 10/2005 |
| CN | 1694338 A | 11/2005 |
| CN | 1705462 A | 12/2005 |
| CN | 1239133 C | 2/2006 |
| CN | 1239209 C | 2/2006 |
| CN | 2754637 Y | 2/2006 |
| CN | 1244381 C | 3/2006 |
| CN | 1249339 C | 4/2006 |
| CN | 2776418 Y | 5/2006 |
| CN | 2787222 Y | 6/2006 |
| CN | 1799652 A | 7/2006 |
| CN | 1806774 A | 7/2006 |
| CN | 1826463 A | 8/2006 |
| CN | 1833735 A | 9/2006 |
| CN | 1833736 A | 9/2006 |
| CN | 2831716 Y | 10/2006 |
| CN | 1874805 A | 12/2006 |
| CN | 1301583 C | 2/2007 |
| CN | 1921947 A | 2/2007 |
| CN | 2880096 Y | 3/2007 |
| CN | 2899800 Y | 5/2007 |
| CN | 101001765 A | 7/2007 |
| CN | 1329666 C | 8/2007 |
| CN | 101024098 A | 8/2007 |
| CN | 101031302 A | 9/2007 |
| CN | 101112628 A | 1/2008 |
| CN | 101121045 A | 2/2008 |
| CN | 101124002 A | 2/2008 |
| CN | 101132830 A | 2/2008 |
| CN | 100382855 C | 4/2008 |
| CN | 101256992 A | 9/2008 |
| CN | 100429406 C | 10/2008 |
| CN | 100439717 C | 12/2008 |
| CN | 100472042 C | 3/2009 |
| CN | 201208423 Y | 3/2009 |
| CN | 100488577 C | 5/2009 |
| CN | 201230980 Y | 5/2009 |
| CN | 201239369 Y | 5/2009 |
| CN | 201246310 Y | 5/2009 |
| CN | 101448535 A | 6/2009 |
| CN | 101522115 A | 9/2009 |
| CN | 101534883 A | 9/2009 |
| CN | 201308666 Y | 9/2009 |
| CN | 101563605 A | 10/2009 |
| CN | 100558416 C | 11/2009 |
| CN | 100566765 C | 12/2009 |
| CN | 101595276 A | 12/2009 |
| CN | 101631578 A | 1/2010 |
| CN | 101652069 A | 2/2010 |
| CN | 101678025 A | 3/2010 |
| CN | 101687791 A | 3/2010 |
| CN | 101244296 B | 6/2010 |
| CN | 101730552 A | 6/2010 |
| CN | 101208058 B | 8/2010 |
| CN | 101808515 A | 8/2010 |
| CN | 101401981 B | 9/2010 |
| CN | 101843528 A | 9/2010 |
| CN | 101232952 B | 11/2010 |
| CN | 101361994 B | 11/2010 |
| CN | 201618200 U | 11/2010 |
| CN | 201710717 U | 1/2011 |
| CN | 101417155 B | 2/2011 |

(56) References Cited

FOREIGN PATENT DOCUMENTS

| | | | |
|---|---|---|---|
| CN | 101581307 B | 4/2011 |
| CN | 102065923 A | 5/2011 |
| CN | 101269245 B | 7/2011 |
| CN | 101618240 B | 8/2011 |
| CN | 102166379 A | 8/2011 |
| CN | 101484093 B | 9/2011 |
| CN | 102292053 A | 12/2011 |
| CN | 102422018 A | 4/2012 |
| CN | 102438673 A | 5/2012 |
| CN | 102475923 A | 5/2012 |
| CN | 202218993 U | 5/2012 |
| CN | 101983732 B | 7/2012 |
| CN | 102553005 A | 7/2012 |
| CN | 101590295 B | 8/2012 |
| CN | 101822854 B | 9/2012 |
| CN | 101822855 B | 9/2012 |
| CN | 101189431 B | 10/2012 |
| CN | 101810891 B | 10/2012 |
| CN | 102711862 A | 10/2012 |
| CN | 102711894 A | 10/2012 |
| CN | 102869318 A | 1/2013 |
| CN | 102917748 A | 2/2013 |
| CN | 102088920 B | 4/2013 |
| CN | 103026234 A | 4/2013 |
| CN | 103068417 A | 4/2013 |
| CN | 103172739 A | 6/2013 |
| CN | 101420993 B | 7/2013 |
| CN | 103206402 A | 7/2013 |
| CN | 103228300 A | 7/2013 |
| CN | 103356306 A | 10/2013 |
| CN | 103381277 A | 11/2013 |
| CN | 103432637 A | 12/2013 |
| CN | 103437951 A | 12/2013 |
| CN | 103446635 A | 12/2013 |
| CN | 103458832 A | 12/2013 |
| CN | 102319457 B | 1/2014 |
| CN | 103509116 A | 1/2014 |
| CN | 103541857 A | 1/2014 |
| CN | 103635212 A | 3/2014 |
| CN | 203507200 U | 4/2014 |
| CN | 203539803 U | 4/2014 |
| CN | 203591299 U | 5/2014 |
| CN | 102317629 B | 8/2014 |
| CN | 203756589 U | 8/2014 |
| CN | 104043153 A | 9/2014 |
| CN | 203829160 U | 9/2014 |
| CN | 104105511 A | 10/2014 |
| CN | 203935281 U | 11/2014 |
| CN | 104185456 A | 12/2014 |
| CN | 104208763 A | 12/2014 |
| CN | 203971002 U | 12/2014 |
| CN | 204050452 U | 12/2014 |
| CN | 102271728 B | 1/2015 |
| CN | 102294057 B | 1/2015 |
| CN | 104271075 A | 1/2015 |
| CN | 102588255 B | 3/2015 |
| CN | 104470454 A | 3/2015 |
| CN | 102300501 B | 4/2015 |
| CN | 103055363 B | 4/2015 |
| CN | 104473676 A | 4/2015 |
| CN | 104524663 A | 4/2015 |
| CN | 204293210 U | 4/2015 |
| CN | 102686316 B | 5/2015 |
| CN | 104586469 A | 5/2015 |
| CN | 104602987 A | 5/2015 |
| CN | 102458275 B | 6/2015 |
| CN | 102458498 B | 6/2015 |
| CN | 104684607 A | 6/2015 |
| CN | 104721899 A | 6/2015 |
| CN | 204419151 U | 6/2015 |
| CN | 102397598 B | 7/2015 |
| CN | 103446634 B | 7/2015 |
| CN | 104758029 A | 7/2015 |
| CN | 104771797 A | 7/2015 |
| CN | 101868628 B | 8/2015 |
| CN | 103706018 B | 9/2015 |
| CN | 104955420 A | 9/2015 |
| CN | 104984425 A | 10/2015 |
| CN | 104997550 A | 10/2015 |
| CN | 105007960 A | 10/2015 |
| CN | 105142719 A | 12/2015 |
| CN | 105208927 A | 12/2015 |
| CN | 102176933 B | 1/2016 |
| CN | 102947092 B | 1/2016 |
| CN | 103717837 B | 1/2016 |
| CN | 105228688 A | 1/2016 |
| CN | 105283149 A | 1/2016 |
| CN | 204972635 U | 1/2016 |
| CN | 103228232 B | 2/2016 |
| CN | 103355925 B | 2/2016 |
| CN | 105311692 A | 2/2016 |
| CN | 102257279 B | 3/2016 |
| CN | 102472719 B | 3/2016 |
| CN | 103154738 B | 3/2016 |
| CN | 105451787 A | 3/2016 |
| CN | 205083494 U | 3/2016 |
| CN | 103850979 B | 4/2016 |
| CN | 105477706 A | 4/2016 |
| CN | 105517589 A | 4/2016 |
| CN | 205163763 U | 4/2016 |
| CN | 103002833 B | 5/2016 |
| CN | 103861163 B | 5/2016 |
| CN | 105555204 A | 5/2016 |
| CN | 205215814 U | 5/2016 |
| CN | 102940911 B | 6/2016 |
| CN | 105641762 A | 6/2016 |
| CN | 105641763 A | 6/2016 |
| CN | 105662439 A | 6/2016 |
| CN | 105709287 A | 6/2016 |
| CN | 105722477 A | 6/2016 |
| CN | 205322884 U | 6/2016 |
| CN | 104069555 B | 7/2016 |
| CN | 105744915 A | 7/2016 |
| CN | 105790453 A | 7/2016 |
| CN | 105792780 A | 7/2016 |
| CN | 105792864 A | 7/2016 |
| CN | 103260666 B | 8/2016 |
| CN | 103732171 B | 8/2016 |
| CN | 103928971 B | 8/2016 |
| CN | 105833370 A | 8/2016 |
| CN | 205411785 U | 8/2016 |
| CN | 205460099 U | 8/2016 |
| CN | 205528886 U | 8/2016 |
| CN | 103889369 B | 9/2016 |
| CN | 104849482 B | 9/2016 |
| CN | 105980660 A | 9/2016 |
| CN | 106075621 A | 11/2016 |
| CN | 106102657 A | 11/2016 |
| CN | 205681272 U | 11/2016 |
| CN | 205698666 U | 11/2016 |
| CN | 205698725 U | 11/2016 |
| CN | 205753678 U | 11/2016 |
| CN | 106214288 A | 12/2016 |
| CN | 106256321 A | 12/2016 |
| CN | 205779766 U | 12/2016 |
| CN | 106334224 A | 1/2017 |
| CN | 205867186 U | 1/2017 |
| CN | 205876589 U | 1/2017 |
| CN | 103281971 B | 2/2017 |
| CN | 106390218 A | 2/2017 |
| CN | 103533970 B | 3/2017 |
| CN | 104826183 B | 3/2017 |
| CN | 106512117 A | 3/2017 |
| CN | 106581840 A | 4/2017 |
| CN | 104068947 B | 5/2017 |
| CN | 106620912 A | 5/2017 |
| CN | 106691363 A | 5/2017 |
| CN | 106716137 A | 5/2017 |
| CN | 106794293 A | 5/2017 |
| CN | 104225696 B | 6/2017 |
| CN | 104918578 B | 6/2017 |
| CN | 105915005 B | 6/2017 |
| CN | 106902404 A | 6/2017 |
| CN | 106955140 A | 7/2017 |

(56) References Cited

FOREIGN PATENT DOCUMENTS

| | | |
|---|---|---|
| CN | 206325049 U | 7/2017 |
| CN | 206355093 U | 7/2017 |
| CN | 105377321 B | 8/2017 |
| CN | 107050543 A | 8/2017 |
| CN | 107050544 A | 8/2017 |
| CN | 107080870 A | 8/2017 |
| CN | 107080871 A | 8/2017 |
| CN | 107110875 A | 8/2017 |
| CN | 206414547 U | 8/2017 |
| CN | 206443963 U | 8/2017 |
| CN | 103930214 B | 9/2017 |
| CN | 104619361 B | 9/2017 |
| CN | 104936550 B | 9/2017 |
| CN | 105188618 B | 9/2017 |
| CN | 107115162 A | 9/2017 |
| CN | 107126299 A | 9/2017 |
| CN | 107126588 A | 9/2017 |
| CN | 107134208 A | 9/2017 |
| CN | 107157623 A | 9/2017 |
| CN | 103857363 B | 10/2017 |
| CN | 104768500 B | 10/2017 |
| CN | 105008841 B | 10/2017 |
| CN | 105492036 B | 10/2017 |
| CN | 107252339 A | 10/2017 |
| CN | 107281567 A | 10/2017 |
| CN | 206592332 U | 10/2017 |
| CN | 107349484 A | 11/2017 |
| CN | 206660203 U | 11/2017 |
| CN | 105287050 B | 12/2017 |
| CN | 105597172 B | 12/2017 |
| CN | 105854097 B | 12/2017 |
| CN | 107412892 A | 12/2017 |
| CN | 107440681 A | 12/2017 |
| CN | 107496054 A | 12/2017 |
| CN | 104602647 B | 1/2018 |
| CN | 106061523 B | 1/2018 |
| CN | 107551341 A | 1/2018 |
| CN | 206934393 U | 1/2018 |
| CN | 107693868 A | 2/2018 |
| CN | 107693869 A | 2/2018 |
| CN | 107708765 A | 2/2018 |
| CN | 207018256 U | 2/2018 |
| CN | 106029120 B | 3/2018 |
| CN | 107753153 A | 3/2018 |
| CN | 107754071 A | 3/2018 |
| CN | 107798980 A | 3/2018 |
| CN | 107835826 A | 3/2018 |
| CN | 107837430 A | 3/2018 |
| CN | 107862963 A | 3/2018 |
| CN | 207125933 U | 3/2018 |
| CN | 207136890 U | 3/2018 |
| CN | 105120796 B | 4/2018 |
| CN | 105214153 B | 4/2018 |
| CN | 107865988 A | 4/2018 |
| CN | 107886825 A | 4/2018 |
| CN | 107913442 A | 4/2018 |
| CN | 107921195 A | 4/2018 |
| CN | 107923311 A | 4/2018 |
| CN | 108025120 A | 5/2018 |
| CN | 108025123 A | 5/2018 |
| CN | 108066834 A | 5/2018 |
| CN | 207410652 U | 5/2018 |
| CN | 104470579 B | 6/2018 |
| CN | 105188604 B | 6/2018 |
| CN | 105492909 B | 6/2018 |
| CN | 105498002 B | 6/2018 |
| CN | 106535824 B | 6/2018 |
| CN | 108136110 A | 6/2018 |
| CN | 108144146 A | 6/2018 |
| CN | 108175884 A | 6/2018 |
| CN | 106028807 B | 7/2018 |
| CN | 106310410 B | 7/2018 |
| CN | 108273148 A | 7/2018 |
| CN | 108310486 A | 7/2018 |
| CN | 108348667 A | 7/2018 |
| CN | 207614108 U | 7/2018 |
| CN | 105640635 B | 8/2018 |
| CN | 105923112 B | 8/2018 |
| CN | 108367106 A | 8/2018 |
| CN | 108430533 A | 8/2018 |
| CN | 108457844 A | 8/2018 |
| CN | 108472138 A | 8/2018 |
| CN | 108472395 A | 8/2018 |
| CN | 108472424 A | 8/2018 |
| CN | 207708246 U | 8/2018 |
| CN | 207708250 U | 8/2018 |
| CN | 105407937 B | 9/2018 |
| CN | 105902298 B | 9/2018 |
| CN | 106420113 B | 9/2018 |
| CN | 106510902 B | 9/2018 |
| CN | 108525039 A | 9/2018 |
| CN | 108525040 A | 9/2018 |
| CN | 108601653 A | 9/2018 |
| CN | 108601872 A | 9/2018 |
| CN | 108601874 A | 9/2018 |
| CN | 108601875 A | 9/2018 |
| CN | 207924984 U | 9/2018 |
| CN | 106377810 B | 10/2018 |
| EP | 96495 B1 | 9/1986 |
| EP | 79373 B1 | 12/1986 |
| EP | 54049 B1 | 1/1988 |
| EP | 292510 A4 | 8/1989 |
| EP | 167562 B1 | 4/1990 |
| EP | 230532 B1 | 9/1990 |
| EP | 241950 B1 | 12/1990 |
| EP | 12977981 | 4/1991 |
| EP | 202649 B1 | 8/1991 |
| EP | 445782 A1 | 9/1991 |
| EP | 464714 A1 | 1/1992 |
| EP | 293592 B1 | 11/1992 |
| EP | 297723 B1 | 8/1993 |
| EP | 396575 B1 | 3/1994 |
| EP | 397668 B1 | 3/1994 |
| EP | 593574 A1 | 4/1994 |
| EP | 378251 B1 | 6/1994 |
| EP | 605621 A1 | 7/1994 |
| EP | 467999 B1 | 8/1994 |
| EP | 350282 B1 | 11/1994 |
| EP | 478635 B1 | 12/1994 |
| EP | 39772081 | 3/1995 |
| EP | 421558 B1 | 4/1995 |
| EP | 364799 B1 | 5/1995 |
| EP | 660726 A1 | 7/1995 |
| EP | 672386 A1 | 9/1995 |
| EP | 349581 B1 | 1/1996 |
| EP | 464973 B1 | 1/1996 |
| EP | 505270 B1 | 1/1996 |
| EP | 583781 B1 | 5/1996 |
| EP | 48010181 | 5/1996 |
| EP | 583012 B1 | 7/1996 |
| EP | 756500 A1 | 2/1997 |
| EP | 0764448 A2 | 3/1997 |
| EP | 767318 A2 | 4/1997 |
| EP | 788808 A2 | 8/1997 |
| EP | 799060 A1 | 10/1997 |
| EP | 823567 A1 | 2/1998 |
| EP | 832357 A1 | 4/1998 |
| EP | 841917 A1 | 5/1998 |
| EP | 560000 B1 | 9/1998 |
| EP | 879012 A1 | 11/1998 |
| EP | 925078 A1 | 6/1999 |
| EP | 807141 B1 | 7/1999 |
| EP | 681654 B1 | 9/1999 |
| EP | 958066 A1 | 11/1999 |
| EP | 964718 A1 | 12/1999 |
| EP | 725657 B1 | 2/2000 |
| EP | 986409 A1 | 3/2000 |
| EP | 1007140 A1 | 6/2000 |
| EP | 1009466 A1 | 6/2000 |
| EP | 1027898 A1 | 8/2000 |
| EP | 1032437 A1 | 9/2000 |
| EP | 1045708 A1 | 10/2000 |
| EP | 1059885 A2 | 12/2000 |
| EP | 746712 B1 | 10/2001 |

(56) References Cited

FOREIGN PATENT DOCUMENTS

| | | |
|---|---|---|
| EP | 1139862 A1 | 10/2001 |
| EP | 1147317 A1 | 10/2001 |
| EP | 1148900 A1 | 10/2001 |
| EP | 699447 B1 | 11/2001 |
| EP | 591896 B1 | 2/2002 |
| EP | 731664 B1 | 2/2002 |
| EP | 79773481 | 2/2002 |
| EP | 1217954 A1 | 7/2002 |
| EP | 1231981 A1 | 8/2002 |
| EP | 950057 B1 | 11/2002 |
| EP | 1278461 A1 | 1/2003 |
| EP | 75176981 | 1/2003 |
| EP | 860046 B1 | 2/2003 |
| EP | 597881 B2 | 3/2003 |
| EP | 732949 B1 | 3/2003 |
| EP | 814701 B1 | 4/2003 |
| EP | 898479 B1 | 5/2003 |
| EP | 905379 B1 | 5/2003 |
| EP | 655625 B1 | 7/2003 |
| EP | 764448 B1 | 7/2003 |
| EP | 768091 B1 | 7/2003 |
| EP | 825888 B1 | 12/2003 |
| EP | 1379197 A1 | 1/2004 |
| EP | 1382366 A1 | 1/2004 |
| EP | 868145 B1 | 2/2004 |
| EP | 895480 B1 | 5/2004 |
| EP | 1441777 A2 | 8/2004 |
| EP | 916359 B1 | 9/2004 |
| EP | 1481698 A2 | 12/2004 |
| EP | 1482999 A1 | 12/2004 |
| EP | 1291027 B1 | 3/2005 |
| EP | 877633 B1 | 7/2005 |
| EP | 611228 B2 | 8/2005 |
| EP | 1212516 B1 | 10/2005 |
| EP | 1597457 A2 | 11/2005 |
| EP | 1261385 B1 | 2/2006 |
| EP | 1648309 A1 | 4/2006 |
| EP | 1354606 B1 | 6/2006 |
| EP | 1663081 A1 | 6/2006 |
| EP | 1321166 B1 | 7/2006 |
| EP | 1191956 B1 | 9/2006 |
| EP | 1722767 A2 | 11/2006 |
| EP | 1070510 B1 | 1/2007 |
| EP | 1317295 B1 | 1/2007 |
| EP | 1327455 B1 | 1/2007 |
| EP | 1776095 A1 | 4/2007 |
| EP | 1141670 B1 | 7/2007 |
| EP | 1807148 A2 | 7/2007 |
| EP | 1827448 A1 | 9/2007 |
| EP | 1374928 B1 | 12/2007 |
| EP | 1877133 A2 | 1/2008 |
| EP | 1379294 B1 | 5/2008 |
| EP | 1930034 A1 | 6/2008 |
| EP | 1318848 B1 | 7/2008 |
| EP | 1356859 B1 | 8/2008 |
| EP | 1955725 A2 | 8/2008 |
| EP | 2058017 A2 | 5/2009 |
| EP | 1731957 B1 | 8/2009 |
| EP | 1173238 B1 | 10/2009 |
| EP | 2043553 B1 | 3/2010 |
| EP | 2158491 A2 | 3/2010 |
| EP | 2178580 A2 | 4/2010 |
| EP | 2182844 A1 | 5/2010 |
| EP | 2194278 A1 | 6/2010 |
| EP | 1471952 B1 | 7/2010 |
| EP | 2207578 A1 | 7/2010 |
| EP | 2216059 A1 | 8/2010 |
| EP | 2218469 A1 | 8/2010 |
| EP | 2219699 A1 | 8/2010 |
| EP | 2222635 A2 | 9/2010 |
| EP | 2222788 A1 | 9/2010 |
| EP | 2229965 A1 | 9/2010 |
| EP | 2235204 A1 | 10/2010 |
| EP | 1280581 B1 | 11/2010 |
| EP | 2246078 A1 | 11/2010 |
| EP | 2248544 A1 | 11/2010 |
| EP | 2252337 A1 | 11/2010 |
| EP | 2266640 A1 | 12/2010 |
| EP | 2269670 A1 | 1/2011 |
| EP | 2297583 A2 | 3/2011 |
| EP | 2298371 A1 | 3/2011 |
| EP | 2298372 A1 | 3/2011 |
| EP | 2298373 A1 | 3/2011 |
| EP | 2299119 A1 | 3/2011 |
| EP | 1464348 B1 | 4/2011 |
| EP | 2314330 A1 | 4/2011 |
| EP | 2314331 A1 | 4/2011 |
| EP | 2338539 A1 | 6/2011 |
| EP | 2338540 A1 | 6/2011 |
| EP | 2338541 A1 | 6/2011 |
| EP | 1654027 B1 | 7/2011 |
| EP | 2343091 A1 | 7/2011 |
| EP | 2347778 A1 | 7/2011 |
| EP | 1812094 B1 | 8/2011 |
| EP | 2349385 A1 | 8/2011 |
| EP | 2353626 A1 | 8/2011 |
| EP | 2356458 A1 | 8/2011 |
| EP | 2363157 A1 | 9/2011 |
| EP | 2366412 A2 | 9/2011 |
| EP | 1907049 B1 | 11/2011 |
| EP | 2388027 A1 | 11/2011 |
| EP | 2388029 A1 | 11/2011 |
| EP | 2399639 A1 | 12/2011 |
| EP | 1514571 B1 | 1/2012 |
| EP | 2407185 A1 | 1/2012 |
| EP | 2407186 A1 | 1/2012 |
| EP | 2407187 A1 | 1/2012 |
| EP | 2422735 A1 | 2/2012 |
| EP | 2322600 B1 | 3/2012 |
| EP | 2429603 A2 | 3/2012 |
| EP | 2459269 A1 | 6/2012 |
| EP | 2497521 A1 | 9/2012 |
| EP | 2140892 B1 | 10/2012 |
| EP | 2505228 A1 | 10/2012 |
| EP | 2150811 B1 | 1/2013 |
| EP | 1833529 B1 | 2/2013 |
| EP | 2554191 A1 | 2/2013 |
| EP | 2277463 B1 | 3/2013 |
| EP | 2564771 A1 | 3/2013 |
| EP | 2151257 B1 | 4/2013 |
| EP | 2575922 A2 | 4/2013 |
| EP | 1623730 B1 | 5/2013 |
| EP | 2606919 A1 | 6/2013 |
| EP | 2606920 A1 | 6/2013 |
| EP | 2607712 A1 | 6/2013 |
| EP | 1919550 B1 | 7/2013 |
| EP | 2620173 A1 | 7/2013 |
| EP | 1331017 B1 | 8/2013 |
| EP | 2101840 B1 | 9/2013 |
| EP | 2401003 B1 | 10/2013 |
| EP | 2654878 A2 | 10/2013 |
| EP | 2654883 A2 | 10/2013 |
| EP | 2671083 A1 | 12/2013 |
| EP | 1412001 B1 | 1/2014 |
| EP | 1942965 B1 | 1/2014 |
| EP | 2231222 B1 | 2/2014 |
| EP | 2697890 A2 | 2/2014 |
| EP | 1017433 B1 | 3/2014 |
| EP | 1629855 B1 | 4/2014 |
| EP | 2736581 A2 | 6/2014 |
| EP | 2744460 A1 | 6/2014 |
| EP | 2745869 A1 | 6/2014 |
| EP | 1485613 B1 | 7/2014 |
| EP | 1605988 B1 | 8/2014 |
| EP | 2792696 A2 | 10/2014 |
| EP | 2195043 B1 | 12/2014 |
| EP | 1962949 B1 | 2/2015 |
| EP | 2030641 B1 | 2/2015 |
| EP | 2643927 B1 | 4/2015 |
| EP | 2868331 A2 | 5/2015 |
| EP | 1460972 B1 | 6/2015 |
| EP | 2150569 B1 | 6/2015 |
| EP | 2152783 B1 | 6/2015 |
| EP | 2345439 B1 | 6/2015 |

(56) References Cited

FOREIGN PATENT DOCUMENTS

| | | |
|---|---|---|
| EP | 2895215 A2 | 7/2015 |
| EP | 1761306 B1 | 8/2015 |
| EP | 2663347 B1 | 8/2015 |
| EP | 2209508 B1 | 9/2015 |
| EP | 2915129 A1 | 9/2015 |
| EP | 2920421 A2 | 9/2015 |
| EP | 2533732 B1 | 11/2015 |
| EP | 1317305 B1 | 12/2015 |
| EP | 1339443 B1 | 1/2016 |
| EP | 2967284 A1 | 1/2016 |
| EP | 2967547 A1 | 1/2016 |
| EP | 2984731 A1 | 2/2016 |
| EP | 2167158 B1 | 3/2016 |
| EP | 2061531 B1 | 4/2016 |
| EP | 2519274 B1 | 4/2016 |
| EP | 1996252 B1 | 5/2016 |
| EP | 2464395 B1 | 5/2016 |
| EP | 3047873 A1 | 7/2016 |
| EP | 3047911 A1 | 7/2016 |
| EP | 2643053 B1 | 8/2016 |
| EP | 2734251 B1 | 8/2016 |
| EP | 3050537 A1 | 8/2016 |
| EP | 1942128 B1 | 9/2016 |
| EP | 2099509 B1 | 9/2016 |
| EP | 2719403 B1 | 9/2016 |
| EP | 3072210 A1 | 9/2016 |
| EP | 3072211 A1 | 9/2016 |
| EP | 2405140 B1 | 10/2016 |
| EP | 2197507 B1 | 11/2016 |
| EP | 2538086 B1 | 11/2016 |
| EP | 3086834 A1 | 11/2016 |
| EP | 2806911 B1 | 12/2016 |
| EP | 3110468 A1 | 1/2017 |
| EP | 3113808 A1 | 1/2017 |
| EP | 3119452 A1 | 1/2017 |
| EP | 3120811 A2 | 1/2017 |
| EP | 3131595 A1 | 2/2017 |
| EP | 3131596 A1 | 2/2017 |
| EP | 3131599 A1 | 2/2017 |
| EP | 3131600 A1 | 2/2017 |
| EP | 3131615 A1 | 2/2017 |
| EP | 2585129 B1 | 3/2017 |
| EP | 2594799 B1 | 3/2017 |
| EP | 3146987 A1 | 3/2017 |
| EP | 3153190 A1 | 4/2017 |
| EP | 3157597 A1 | 4/2017 |
| EP | 3173110 A1 | 5/2017 |
| EP | 2825107 B1 | 7/2017 |
| EP | 3185924 A1 | 7/2017 |
| EP | 3185925 A1 | 7/2017 |
| EP | 3189526 A1 | 7/2017 |
| EP | 3191164 A1 | 7/2017 |
| EP | 2618001 B1 | 8/2017 |
| EP | 3197602 A1 | 8/2017 |
| EP | 3198677 A1 | 8/2017 |
| EP | 3204989 A1 | 8/2017 |
| EP | 3212250 A1 | 9/2017 |
| EP | 3219339 A1 | 9/2017 |
| EP | 3223880 A1 | 10/2017 |
| EP | 3232948 A1 | 10/2017 |
| EP | 1885409 B1 | 11/2017 |
| EP | 2292282 B1 | 11/2017 |
| EP | 2945661 B1 | 11/2017 |
| EP | 3238764 A1 | 11/2017 |
| EP | 3244814 A1 | 11/2017 |
| EP | 3247420 A1 | 11/2017 |
| EP | 3247421 A2 | 11/2017 |
| EP | 3248628 A1 | 11/2017 |
| EP | 2136861 B1 | 12/2017 |
| EP | 3256183 A1 | 12/2017 |
| EP | 3256184 A1 | 12/2017 |
| EP | 3256185 A1 | 12/2017 |
| EP | 3256186 A1 | 12/2017 |
| EP | 3007742 B1 | 1/2018 |
| EP | 3277200 A1 | 2/2018 |
| EP | 3287155 A1 | 2/2018 |
| EP | 2482916 B1 | 3/2018 |
| EP | 2948202 B1 | 3/2018 |
| EP | 3294367 A1 | 3/2018 |
| EP | 2945662 B1 | 4/2018 |
| EP | 3310409 A1 | 4/2018 |
| EP | 3222301 B1 | 5/2018 |
| EP | 3222302 B1 | 5/2018 |
| EP | 3313471 A1 | 5/2018 |
| EP | 3324840 A1 | 5/2018 |
| EP | 3325035 A1 | 5/2018 |
| EP | 3326487 A1 | 5/2018 |
| EP | 1789129 B1 | 6/2018 |
| EP | 1990358 B1 | 6/2018 |
| EP | 3329953 A1 | 6/2018 |
| EP | 3335647 A2 | 6/2018 |
| EP | 3341069 A1 | 7/2018 |
| EP | 3349839 A1 | 7/2018 |
| EP | 2219698 B1 | 8/2018 |
| EP | 2890420 B1 | 8/2018 |
| EP | 3352808 A1 | 8/2018 |
| EP | 3352835 A1 | 8/2018 |
| EP | 3360233 A1 | 8/2018 |
| EP | 3360515 A1 | 8/2018 |
| EP | 1534381 B1 | 9/2018 |
| EP | 3108909 B1 | 9/2018 |
| EP | 3377001 A1 | 9/2018 |
| EP | 3377002 A1 | 9/2018 |
| EP | 3377134 A1 | 9/2018 |
| EP | 3377135 A1 | 9/2018 |
| EP | 3377136 A1 | 9/2018 |
| EP | 2249746 B1 | 10/2018 |
| EP | 2988795 B1 | 10/2018 |
| EP | 3383300 A1 | 10/2018 |
| EP | 3383448 A1 | 10/2018 |
| EP | 3388005 A1 | 10/2018 |
| EP | 3542835 A1 | 9/2019 |
| FR | 2331995 A2 | 6/1977 |
| JP | 64-52472 A | 2/1989 |
| JP | 02289241 | 11/1990 |
| JP | 04176471 A | 6/1992 |
| JP | 04224760 A | 8/1992 |
| JP | H05-078996 U | 10/1993 |
| JP | H11-062856 A | 3/1999 |
| JP | 02888609 B2 | 5/1999 |
| JP | 02927460 B2 | 7/1999 |
| JP | H11-244376 A | 9/1999 |
| JP | 2000102604 A | 4/2000 |
| JP | 2000107281 A | 4/2000 |
| JP | 2000283062 A | 10/2000 |
| JP | 03131696 B2 | 2/2001 |
| JP | 2001061957 A | 3/2001 |
| JP | 2001090687 A | 4/2001 |
| JP | 03174338 B2 | 6/2001 |
| JP | 2001173402 A | 6/2001 |
| JP | 2001523983 A | 11/2001 |
| JP | 03278160 B2 | 4/2002 |
| JP | 2002191123 A | 7/2002 |
| JP | 03313061 B2 | 8/2002 |
| JP | 2003047656 A | 2/2003 |
| JP | 2003070906 A | 3/2003 |
| JP | 2003205030 A | 7/2003 |
| JP | 2004011525 A | 1/2004 |
| JP | 2004016426 A | 1/2004 |
| JP | 2004028102 A | 1/2004 |
| JP | 2004073400 A | 3/2004 |
| JP | 2004209240 A | 7/2004 |
| JP | 2004278375 A | 10/2004 |
| JP | 03612581 B2 | 1/2005 |
| JP | 2005058617 A | 3/2005 |
| JP | 2005192687 A | 7/2005 |
| JP | 2005199076 A | 7/2005 |
| JP | 2005348996 A | 12/2005 |
| JP | 2006000631 A | 1/2006 |
| JP | 03786289 B2 | 6/2006 |
| JP | 03803417 B2 | 8/2006 |
| JP | 2006280571 A | 10/2006 |
| JP | 03854972 B2 | 12/2006 |
| JP | 2007044302 A | 2/2007 |

(56) References Cited

FOREIGN PATENT DOCUMENTS

| | | |
|---|---|---|
| JP | 2007075541 A | 3/2007 |
| JP | 2007089607 A | 4/2007 |
| JP | 2007089973 A | 4/2007 |
| JP | 2007222670 A | 9/2007 |
| JP | 2007236564 A | 9/2007 |
| JP | 04016441 B2 | 12/2007 |
| JP | 04022372 B2 | 12/2007 |
| JP | 2008018242 A | 1/2008 |
| JP | 04051812 B2 | 2/2008 |
| JP | 04072721 B2 | 4/2008 |
| JP | 04077902 B2 | 4/2008 |
| JP | 04078245 B2 | 4/2008 |
| JP | 04084060 B2 | 4/2008 |
| JP | 04086185 B2 | 5/2008 |
| JP | 04108054 B2 | 6/2008 |
| JP | 04121709 B2 | 7/2008 |
| JP | 04163384 B2 | 10/2008 |
| JP | 04179634 B2 | 11/2008 |
| JP | 2008264586 A | 11/2008 |
| JP | 04198986 B2 | 12/2008 |
| JP | 04209412 B2 | 1/2009 |
| JP | 2009090882 A | 4/2009 |
| JP | 04279494 B2 | 6/2009 |
| JP | 04308723 B2 | 8/2009 |
| JP | 2009178570 A | 8/2009 |
| JP | 2009254436 A | 11/2009 |
| JP | 2009273214 A | 11/2009 |
| JP | 04387106 B2 | 12/2009 |
| JP | 04391680 B2 | 12/2009 |
| JP | 04414925 B2 | 2/2010 |
| JP | 04440499 B2 | 3/2010 |
| JP | 04467187 B2 | 5/2010 |
| JP | 04468965 B2 | 5/2010 |
| JP | 04484320 B2 | 6/2010 |
| JP | 04512150 B2 | 7/2010 |
| JP | 2010158532 A | 7/2010 |
| JP | 04523961 B2 | 8/2010 |
| JP | 04523962 B2 | 8/2010 |
| JP | 04548450 B2 | 9/2010 |
| JP | 04549407 B2 | 9/2010 |
| JP | 2010246941 A | 11/2010 |
| JP | 04611364 B2 | 1/2011 |
| JP | 04611365 B2 | 1/2011 |
| JP | 04646393 B2 | 3/2011 |
| JP | 04655231 B2 | 3/2011 |
| JP | 04656332 B2 | 3/2011 |
| JP | 04674978 B2 | 4/2011 |
| JP | 2011072533 A | 4/2011 |
| JP | 2011116765 A | 6/2011 |
| JP | 04728351 B2 | 7/2011 |
| JP | 04741242 B2 | 8/2011 |
| JP | 04741489 B2 | 8/2011 |
| JP | 2011161401 A | 8/2011 |
| JP | 04795536 B2 | 10/2011 |
| JP | 04851333 B2 | 1/2012 |
| JP | 04865825 B2 | 2/2012 |
| JP | 04881154 B2 | 2/2012 |
| JP | 04897811 B2 | 3/2012 |
| JP | 04907028 B2 | 3/2012 |
| JP | 04908737 B2 | 4/2012 |
| JP | 04964854 B2 | 7/2012 |
| JP | 04987999 B2 | 8/2012 |
| JP | 05047447 B2 | 10/2012 |
| JP | 05048749 B2 | 10/2012 |
| JP | 05093869 B2 | 12/2012 |
| JP | 05102033 B2 | 12/2012 |
| JP | 05164558 B2 | 3/2013 |
| JP | 05185629 B2 | 4/2013 |
| JP | 05193059 B2 | 5/2013 |
| JP | 05197636 B2 | 5/2013 |
| JP | 2013078564 A | 5/2013 |
| JP | 05215580 B2 | 6/2013 |
| JP | 05267227 B2 | 8/2013 |
| JP | 05286268 B2 | 9/2013 |
| JP | 2013192711 A | 9/2013 |
| JP | 2014004303 A | 1/2014 |
| JP | 05427620 B2 | 2/2014 |
| JP | 05429714 B2 | 2/2014 |
| JP | 05440528 B2 | 3/2014 |
| JP | 05440529 B2 | 3/2014 |
| JP | 05461710 B2 | 4/2014 |
| JP | 05500348 B2 | 5/2014 |
| JP | 2014091049 A | 5/2014 |
| JP | 2014114784 A | 6/2014 |
| JP | 05539484 B2 | 7/2014 |
| JP | 05557175 B2 | 7/2014 |
| JP | 05590213 B2 | 9/2014 |
| JP | 05596974 B2 | 10/2014 |
| JP | 05611948 B2 | 10/2014 |
| JP | 05633512 B2 | 12/2014 |
| JP | 05656835 B2 | 1/2015 |
| JP | 05673795 B2 | 2/2015 |
| JP | 05675786 B2 | 2/2015 |
| JP | 05676118 B2 | 2/2015 |
| JP | 05701848 B2 | 4/2015 |
| JP | 05711245 B2 | 4/2015 |
| JP | 05750492 B2 | 7/2015 |
| JP | 05781597 B2 | 9/2015 |
| JP | 2015159947 A | 9/2015 |
| JP | 05837162 B2 | 12/2015 |
| JP | 05868180 B2 | 2/2016 |
| JP | 05894116 B2 | 3/2016 |
| JP | 05894678 B2 | 3/2016 |
| JP | 2016028764 A | 3/2016 |
| JP | 2016182342 A | 10/2016 |
| JP | 06034858 B2 | 11/2016 |
| JP | 06038018 B2 | 12/2016 |
| JP | 06054106 B2 | 12/2016 |
| JP | 2016202553 A | 12/2016 |
| JP | 06083929 B2 | 2/2017 |
| JP | 2017035323 A | 2/2017 |
| JP | 2017517306 A | 6/2017 |
| JP | 2017127675 A | 7/2017 |
| JP | 06178666 B2 | 8/2017 |
| JP | 2017159083 A | 9/2017 |
| JP | 06220867 B2 | 10/2017 |
| JP | 06236451 B2 | 11/2017 |
| JP | 06267625 B2 | 1/2018 |
| JP | 2018020199 A | 2/2018 |
| JP | 06295204 B2 | 3/2018 |
| JP | 06329358 B2 | 5/2018 |
| JP | 06339371 B2 | 6/2018 |
| JP | 06345112 B2 | 6/2018 |
| JP | 06353787 B2 | 7/2018 |
| JP | 06382285 B2 | 8/2018 |
| JP | 2018122146 A | 8/2018 |
| JP | 2018523541 A | 8/2018 |
| WO | WO87/002894 A2 | 5/1987 |
| WO | WO88/009874 A1 | 12/1988 |
| WO | WO92/002263 A1 | 2/1992 |
| WO | WO92/003181 A1 | 3/1992 |
| WO | WO96/14027 A1 | 5/1995 |
| WO | WO95/031196 A1 | 11/1995 |
| WO | WO96/016684 A1 | 6/1996 |
| WO | WO98/042984 A1 | 10/1998 |
| WO | WO00/019097 A1 | 4/2000 |
| WO | WO00/027446 A1 | 5/2000 |
| WO | WO00/035515 A1 | 6/2000 |
| WO | WO01/017581 A2 | 3/2001 |
| WO | WO01/019444 A1 | 3/2001 |
| WO | WO01/041070 A1 | 6/2001 |
| WO | WO01/074419 A1 | 10/2001 |
| WO | WO01/087176 A1 | 11/2001 |
| WO | WO01/095813 A1 | 12/2001 |
| WO | WO02/47751 A2 | 6/2002 |
| WO | WO02/053226 A2 | 7/2002 |
| WO | WO02/070039 A2 | 9/2002 |
| WO | WO02/072000 A1 | 9/2002 |
| WO | WO02/081021 A1 | 10/2002 |
| WO | WO03/024501 A2 | 3/2003 |
| WO | WO03/061727 A2 | 7/2003 |
| WO | WO03/094716 A1 | 11/2003 |
| WO | WO03/103745 A2 | 12/2003 |
| WO | WO2004/026394 A1 | 4/2004 |

(56) References Cited

FOREIGN PATENT DOCUMENTS

| | | |
|---|---|---|
| WO | WO2004/034034 A1 | 4/2004 |
| WO | WO2004/088480 A2 | 10/2004 |
| WO | WO2004/098677 A1 | 11/2004 |
| WO | WO2005/020848 A2 | 3/2005 |
| WO | WO2005/033671 A1 | 4/2005 |
| WO | WO2005/037348 A1 | 4/2005 |
| WO | WO2005/054680 A1 | 6/2005 |
| WO | WO2005/108796 A1 | 11/2005 |
| WO | WO2006/040252 A1 | 4/2006 |
| WO | WO2006/053384 A1 | 5/2006 |
| WO | WO2006/081255 A2 | 8/2006 |
| WO | WO2006/121698 A2 | 11/2006 |
| WO | WO2007/008907 A2 | 1/2007 |
| WO | WO2007/033933 A1 | 3/2007 |
| WO | WO2007/053881 A1 | 5/2007 |
| WO | WO2007/065408 A2 | 6/2007 |
| WO | WO2007/092494 A2 | 8/2007 |
| WO | WO2007/105842 A1 | 9/2007 |
| WO | WO2007/146231 A2 | 12/2007 |
| WO | WO2008/005747 A2 | 1/2008 |
| WO | WO2008/008427 A2 | 1/2008 |
| WO | WO2008/088874 A2 | 7/2008 |
| WO | WO2008/102015 A1 | 8/2008 |
| WO | WO2008/121143 A1 | 10/2008 |
| WO | WO2008/121145 A1 | 10/2008 |
| WO | WO2008/137237 A2 | 11/2008 |
| WO | WO2008/140034 A1 | 11/2008 |
| WO | WO2009/017549 A1 | 2/2009 |
| WO | WO2009035581 A1 | 3/2009 |
| WO | WO2009/046789 A1 | 4/2009 |
| WO | WO2009/075668 A2 | 6/2009 |
| WO | WO2009/096991 A1 | 8/2009 |
| WO | WO2010/025411 A2 | 3/2010 |
| WO | WO2010/119110 A1 | 10/2010 |
| WO | WO2011/003043 A1 | 1/2011 |
| WO | WO2011/024928 A1 | 3/2011 |
| WO | WO2011/035925 A1 | 3/2011 |
| WO | WO2011/039091 A1 | 4/2011 |
| WO | WO2011/081629 A1 | 7/2011 |
| WO | WO2011/082212 A1 | 7/2011 |
| WO | WO2011/085040 A1 | 7/2011 |
| WO | WO2011/117566 A1 | 9/2011 |
| WO | WO2011/119060 A2 | 9/2011 |
| WO | WO2012/037506 A2 | 3/2012 |
| WO | WO2012/051454 A2 | 4/2012 |
| WO | WO2012/064674 A1 | 5/2012 |
| WO | WO2012/075152 A1 | 6/2012 |
| WO | WO2012/075262 A1 | 6/2012 |
| WO | WO2012/087811 A2 | 6/2012 |
| WO | WO2012/094535 A2 | 7/2012 |
| WO | WO2012/094641 A2 | 7/2012 |
| WO | WO2012/096716 A2 | 7/2012 |
| WO | WO2012/112129 A1 | 8/2012 |
| WO | WO2013/034547 A1 | 3/2013 |
| WO | WO2013/093058 A1 | 6/2013 |
| WO | WO2013/127182 A1 | 9/2013 |
| WO | WO2013/134319 A1 | 9/2013 |
| WO | WO2013/148560 A1 | 10/2013 |
| WO | WO2013/148697 A1 | 10/2013 |
| WO | WO2014/070458 A1 | 5/2014 |
| WO | WO2014/096408 A1 | 6/2014 |
| WO | WO2014/106635 A1 | 7/2014 |
| WO | WO2014/116639 A1 | 7/2014 |
| WO | WO2014/142754 A1 | 9/2014 |
| WO | WO2014/143593 A1 | 9/2014 |
| WO | WO2014/164136 A1 | 10/2014 |
| WO | WO2014/164292 A1 | 10/2014 |
| WO | WO2014/166128 A1 | 10/2014 |
| WO | WO2014/169023 A2 | 10/2014 |
| WO | WO2015/119705 A1 | 8/2015 |
| WO | WO2015/160943 A1 | 10/2015 |
| WO | WO2015/160979 A1 | 10/2015 |
| WO | WO2015/171156 A1 | 11/2015 |
| WO | WO2015/175711 A1 | 11/2015 |
| WO | WO2015/175718 A1 | 11/2015 |
| WO | WO2015/177793 A2 | 11/2015 |
| WO | WO2015/187659 A2 | 12/2015 |
| WO | WO2016/100600 A2 | 6/2016 |
| WO | WO2016/113266 A1 | 7/2016 |
| WO | WO2016/116630 A2 | 7/2016 |
| WO | WO2017/001358 A1 | 1/2017 |
| WO | WO2017/011257 A1 | 1/2017 |
| WO | WO2017/032751 A1 | 3/2017 |
| WO | WO2017/048733 A1 | 3/2017 |
| WO | WO2017/060254 A1 | 4/2017 |
| WO | WO2017/060257 A1 | 4/2017 |
| WO | WO2017/075322 A1 | 5/2017 |
| WO | WO2017/087380 A1 | 5/2017 |
| WO | WO2017/120453 A1 | 7/2017 |
| WO | WO2017/133425 A1 | 8/2017 |
| WO | WO2017/134657 A1 | 8/2017 |
| WO | WO2017/139113 A1 | 8/2017 |
| WO | WO2017/139246 A1 | 8/2017 |
| WO | WO2017/147082 A1 | 8/2017 |
| WO | WO2017/147103 A1 | 8/2017 |
| WO | WO2017/147291 A1 | 8/2017 |
| WO | WO2017/151987 A1 | 9/2017 |
| WO | WO2017/156386 A1 | 9/2017 |
| WO | WO2017/159849 A1 | 9/2017 |
| WO | WO2017/165372 A1 | 9/2017 |
| WO | WO2017/178904 A1 | 10/2017 |
| WO | WO2017/183124 A1 | 10/2017 |
| WO | WO2017/190155 A2 | 11/2017 |
| WO | WO2017/192119 A1 | 11/2017 |
| WO | WO2017/196271 A1 | 11/2017 |
| WO | WO2017/205909 A1 | 12/2017 |
| WO | WO2017/210318 A2 | 12/2017 |
| WO | WO2017/214118 A1 | 12/2017 |
| WO | WO2017/214183 A1 | 12/2017 |
| WO | WO2017/217946 A1 | 12/2017 |
| WO | WO2018/007120 A1 | 1/2018 |
| WO | WO2018/007471 A1 | 1/2018 |
| WO | WO2018/017678 A1 | 1/2018 |
| WO | WO2018/017683 A1 | 1/2018 |
| WO | WO2018/017716 A1 | 1/2018 |
| WO | WO2018/026764 A1 | 2/2018 |
| WO | WO2018/026769 A1 | 2/2018 |
| WO | WO2018/031741 A1 | 2/2018 |
| WO | WO2018/035069 A1 | 2/2018 |
| WO | WO2018/039124 A1 | 3/2018 |
| WO | WO2018/039326 A1 | 3/2018 |
| WO | WO2018/041963 A1 | 3/2018 |
| WO | WO2018/045299 A1 | 3/2018 |
| WO | WO2018/051091 A1 | 3/2018 |
| WO | WO2018/052482 A1 | 3/2018 |
| WO | WO2018/057482 A1 | 3/2018 |
| WO | WO2018/057563 A1 | 3/2018 |
| WO | WO2018/061002 A1 | 4/2018 |
| WO | WO2018/064437 A1 | 4/2018 |
| WO | WO2018/067410 A1 | 4/2018 |
| WO | WO2018/073150 A1 | 4/2018 |
| WO | WO2018/078370 A1 | 5/2018 |
| WO | WO2018/078615 A1 | 5/2018 |
| WO | WO2018/082987 A1 | 5/2018 |
| WO | WO2018/088939 A1 | 5/2018 |
| WO | WO2018/089970 A1 | 5/2018 |
| WO | WO2018/093663 A1 | 5/2018 |
| WO | WO2018/096531 A1 | 5/2018 |
| WO | WO2018/118756 A1 | 6/2018 |
| WO | WO2018/132181 A1 | 7/2018 |
| WO | WO2018/132182 A1 | 7/2018 |
| WO | WO2018/135477 A1 | 7/2018 |
| WO | WO2018/135478 A1 | 7/2018 |
| WO | WO2018/136592 A2 | 7/2018 |
| WO | WO2018/139508 A1 | 8/2018 |
| WO | WO2018/145434 A1 | 8/2018 |
| WO | WO2018/146045 A1 | 8/2018 |
| WO | WO2018/146170 A1 | 8/2018 |
| WO | WO2018/146173 A1 | 8/2018 |
| WO | WO2018/146177 A1 | 8/2018 |
| WO | WO2018/148456 A1 | 8/2018 |
| WO | WO2018/156524 A1 | 8/2018 |
| WO | WO2018/158636 A1 | 9/2018 |
| WO | WO2018/177344 A1 | 10/2018 |

(56) References Cited

FOREIGN PATENT DOCUMENTS

| | | | |
|---|---|---|---|
| WO | WO2018/178939 A1 | 10/2018 |
| WO | WO2018/183128 A1 | 10/2018 |
| WO | WO2018/187576 A2 | 10/2018 |
| WO | WO2018/226991 A1 | 12/2018 |
| WO | WO2019/094963 A1 | 5/2019 |
| WO | WO2019/138350 A2 | 7/2019 |
| WO | WO2019/158996 A1 | 8/2019 |
| WO | WO2019/191851 A1 | 9/2019 |
| WO | WO2019/194956 A1 | 10/2019 |
| WO | WO2019/229222 A1 | 12/2019 |
| WO | WO2020/028537 A1 | 2/2020 |
| WO | WO2020/0234785 A1 | 11/2020 |
| WO | WO2021/026469 A1 | 2/2021 |
| WO | WO2021/026472 A1 | 2/2021 |
| WO | WO2021/062260 A1 | 4/2021 |
| WO | WO2021/062265 A1 | 4/2021 |
| WO | WO2021/062270 A1 | 4/2021 |
| WO | WO2021/119478 A1 | 6/2021 |
| WO | WO2021/127503 A1 | 6/2021 |
| WO | WO2021/158967 A1 | 8/2021 |
| WO | WO2021/195617 A1 | 9/2021 |
| WO | WO2021/222403 A1 | 11/2021 |
| WO | WO2021/231574 A1 | 11/2021 |
| WO | WO2021/243263 A1 | 12/2021 |
| WO | WO2022/072944 A1 | 4/2022 |
| WO | WO2022/076862 A1 | 4/2022 |
| WO | WO2022/076948 A1 | 4/2022 |
| WO | WO2022/120270 A1 | 6/2022 |

OTHER PUBLICATIONS

Brandt et al.; U.S. Appl. No. 18/554,756 entitled "Catheter blood pump shrouds and assembly thereof," filed Oct. 10, 2023.

Ryan et al.; U.S. Appl. No. 18/559,231 entitled "Intravascular blood pump outflow flow disruptor," filed Nov. 6, 2023.

Salahieh et al.; U.S. Appl. No. 18/615,896 entitled "Intravascular blood pumps and methods of use and manufacture," filed Mar. 25, 2024.

Varghai et al.; U.S. Appl. No. 18/711,528 entitled "Intravascular blood pumps, motors, and fluid control," filed May 17, 2024.

Hildebrand; U.S. Appl. No. 18/710,551 entitled "Intravascular blood pumps and expandable scaffolds with stiffening members" filed May 15, 2024.

Jagani et al.; Dual-propeller cavopulmonary pump for assisting patients with hypoplastic right ventricle; ASAIO Journal (American Society for Artificial Internal Organs); 10 pages; DOI: 10.1097/MAT.0000000000000907; Jan. 2019.

Park et al.; Biologically Inspired, Open, Helicoid Impeller Design for Mechanical Circulatory Assist; ASAIO Journal (American Society for Artificial Internal Organs); DOI: 10.1097/MAT.0000000000001090; Oct. 23, 2019.

Reitan et al.; First human use of the reitan catheter pump; Asaio Journal; 47(2); p. 124; Mar.-Apr. 2001.

Gupta et al.; U.S. Appl. No. 29/761,852 entitled "Intravascular blood pump external display screen or a portion thereof with graphical user interface," filed Dec. 11, 2020.

Hildebrand et al.; U.S. Appl. No. 17/632,550 entitled Catheter blood pumps and impellers, filed Feb. 3, 2022.

Saul et al.; U.S. Appl. No. 17/998,614 entitled "Inflatable medical devices, methods of manufacture and use," filed Nov. 11, 2022.

Ryan et al.; U.S. Appl. No. 17/998,624 entitled "Catheter blood pumps and collapsible pump housings," filed Nov. 11, 2022.

Varghai et al.; U.S. Appl. No. 18/000,265 entitled "Intravascular blood pumps ," filed Nov. 29, 2022.

Varghai et al.; U.S. Appl. No. 17/794,002 entitled "Intravascular blood pumps, motors, and fluid control," filed Jul. 20, 2022.

Hildebrand et al.; U.S. Appl. No. 17/907,321 entitled "Intravascular blood pumps," filed Sep. 26, 2022.

Salahieh et al.; U.S. Appl. No. 18/047,076 entitled "Intravascular fluid movement devices, systems, and methods of use," filed Oct. 17, 2022.

Merchant et al.; U.S. Appl. No. 17/997,489 entitled "Intravascular blood pumps and control thereof," filed Oct. 28, 2022.

Ryan et al.; U.S. Appl. No. 17/782,675 entitled "Intravascular blood pumps, motors, and fluid control," filed Jun. 6, 2022.

\* cited by examiner

DESCENDING AORTA AND VENA CAVA BLOOD PUMPS

CROSS REFERENCE TO RELATED APPLICATIONS

This application claims the benefit of priority of U.S. Provisional App. No. 62/946,927, filed Dec. 11, 2019, and U.S. Provisional App. No. 62/951,519, filed Dec. 20, 2019, the complete disclosures of which are incorporated by reference herein for all purposes.

INCORPORATION BY REFERENCE

All publications and patent applications mentioned in this specification are herein incorporated by reference to the same extent as if each individual publication or patent application was specifically and individually indicated to be incorporated by reference.

The following publications are incorporated by reference herein for all purposes: WO2018/226991A1, WO2019/094963A1, WO2019/152875A1, WO2020/028537A1, WO2020/073047A1, WO2018/226991A1, WO2019/094963A1, WO2019/152875A1, U.S. Pat. No. 9,572,915, and US 2017/0100527.

BACKGROUND

Descriptions have been presented that attempt to increase renal artery and kidney perfusion using a blood pump positioned in a descending aorta. One or more aspects of those descriptions, however, may have deficiencies that can be addressed by catheter-based blood pumps and methods of placement and use that are set forth herein.

Additionally, descriptions have been presented that attempt to reduce blood pressure within one or more renal vein by placing a blood pump in a vena cava and pumping blood away from the region. One or more aspects of those descriptions, however, may have deficiencies that can be addressed by catheter-based blood pumps and methods of placement and use that are set forth herein.

SUMMARY OF THE DISCLOSURE

One aspect of the disclosure is a method of supporting circulation in a descending aorta of a subject. The method may include advancing an expandable pump portion of a blood pump into a descending aorta of a subject, the pump portion comprising an expandable blood conduit between a pump inflow and a pump outflow, the pump portion further including first and second expandable impellers at least partially within the blood conduit. The method may further include expanding the expandable blood conduit to an expanded and deployed configuration within the descending aorta. The method may further include expanding the first expandable impeller into an expanded configuration at least partially within the blood conduit and expanding the second expandable impeller into an expanded configuration at least partially within the blood conduit, and rotating the first and second expandable impellers to thereby move blood into the pump, through the blood conduit, and out of the pump. The rotating step may move blood through the blood conduit at a rate of at least 3.5 L/min.

In this aspect, the rotating step may cause the pump outflow to include a radial flow component.

In this aspect, moving blood out of the pump outflow may perfuse at least one renal artery.

In this aspect, expanding the expandable blood conduit may comprise expanding the expandable blood conduit to a deployed configuration within the descending aorta such that the pump outflow is upstream or aligned with a renal artery, and wherein the outflow is at least partially directed radially into the renal artery due to the position of the blood conduit in the descending aorta.

In this aspect, expanding the expandable blood conduit to a deployed configuration within the descending aorta may comprise expanding the expandable blood conduit to a deployed configuration near a renal artery such that the pump outflow perfuses at least one renal artery.

In this aspect, expanding the second expandable impeller may comprise expanding the second expandable impeller into an expanded configuration such that at least a portion of the second expandable impeller is extending beyond a proximal end of the blood conduit, and wherein the outflow may have a radial flow component due at least partially to the portion of the second expandable impeller that is extending beyond a proximal end of the blood conduit.

In this aspect, expanding the expandable blood conduit within the descending aorta may comprise expanding a distal scaffold to an expandable configuration that provides radial support to the blood conduit at the location of the first impeller. Expanding the expandable blood conduit within the descending aorta may comprise expanding a proximal scaffold to an expandable configuration that provides radial support to the blood conduit at the location of the second impeller.

In this aspect, expanding the expandable blood conduit may comprise expanding a central region of the blood conduit that is between the first and second impellers, wherein the central region may be more flexible than regions of the blood conduit that surround the first and second impellers.

In this aspect, expanding the expandable blood conduit to a deployed configuration within the descending aorta may comprise expanding the expandable blood conduit to a deployed configuration within the descending thoracic aorta.

One aspect of this disclosure is a method of supporting circulation in a descending aorta of a subject. The method may include advancing an expandable pump portion of a blood pump into a descending aorta of a subject, the pump portion including a distal impeller and a proximal impeller; expanding a distal expandable blood conduit into an expanded configuration aligned with or upstream to a renal artery; expanding the distal impeller to an expanded configuration at least partially within the distal expandable blood conduit; expanding a proximal expandable blood conduit into an expanded configuration downstream from the renal artery; expanding the proximal impeller to an expanded configuration at least partially within the proximal expandable blood conduit; rotating the distal impeller to move blood into a distal end of the distal expandable blood conduit, through the distal expandable blood conduit, and out of a proximal end of the distal expandable blood conduit; and rotating the proximal impeller to move blood through the proximal expandable blood conduit.

In this aspect, rotating the distal impeller may cause blood to move out of the proximal end of the distal expandable blood conduit and perfuse the renal artery, optionally also perfusing a second renal artery.

In this aspect, rotating distal and proximal impellers may move blood past the distal and proximal impellers in an antegrade direction.

In this aspect, rotating the distal impeller may move blood past the distal impeller in an antegrade direction, and rotating the proximal impeller may move blood past the proximal impeller in a retrograde direction toward the renal artery.

In this aspect, rotating the distal and proximal impellers may be performed discontinuously and in a manner that is related to one or more aspects of the subject's cardiac cycle.

In this aspect, rotating the distal and proximal impellers may occur during at least a portion of systole, and wherein the distal and proximal impellers may not be rotated during at least a portion of diastole, optionally during any of diastole.

In this aspect, rotating the proximal impeller may move blood into a distal end of the proximal expandable blood conduit, through the proximal expandable blood conduit, and out of a proximal end of the proximal expandable blood conduit.

In this aspect, expanding a distal expandable blood conduit into an expanded configuration aligned with or upstream to a renal artery may comprise expanding a distal expandable scaffold.

In this aspect, expanding a proximal expandable blood conduit may comprise expanding a proximal expandable scaffold.

In this aspect, rotating the distal and proximal impellers may be performed by rotating a common drive mechanism to which the distal and proximal impellers are in rotational communication.

In this aspect, the method may further comprise causing blood to flow radially outward from a proximal end of the distal blood conduit.

One aspect of the disclosure is a method of supporting circulation in proximity to renal veins. The method may include advancing an expandable pump portion of a blood pump into an inferior vena cava ("IVC") of a subject, the pump portion comprising an expandable blood conduit between a proximal end and a distal end, the pump portion further including first and second expandable impellers; expanding the expandable blood conduit to a deployed configuration within the IVC; expanding the first expandable impeller into an expanded configuration at least partially within the blood conduit; expanding the second expandable impeller into an expanded configuration at least partially within the blood conduit; and rotating the first and second expandable impellers to move blood into the blood conduit, through the blood conduit, and out of the blood conduit. This aspect may additionally include any other suitable method step described herein.

DETAILED DESCRIPTION

The disclosure is related to catheter blood pumps that may be placed in one or more of the following locations: a descending aorta, an inferior vena cava ("IVC"), a renal artery, or a renal vein. The blood pumps herein may include pump portions that include one or more impellers within a blood conduit, wherein the one or more impellers are sized and configured to move blood through the blood conduit when rotated.

Figure 1:
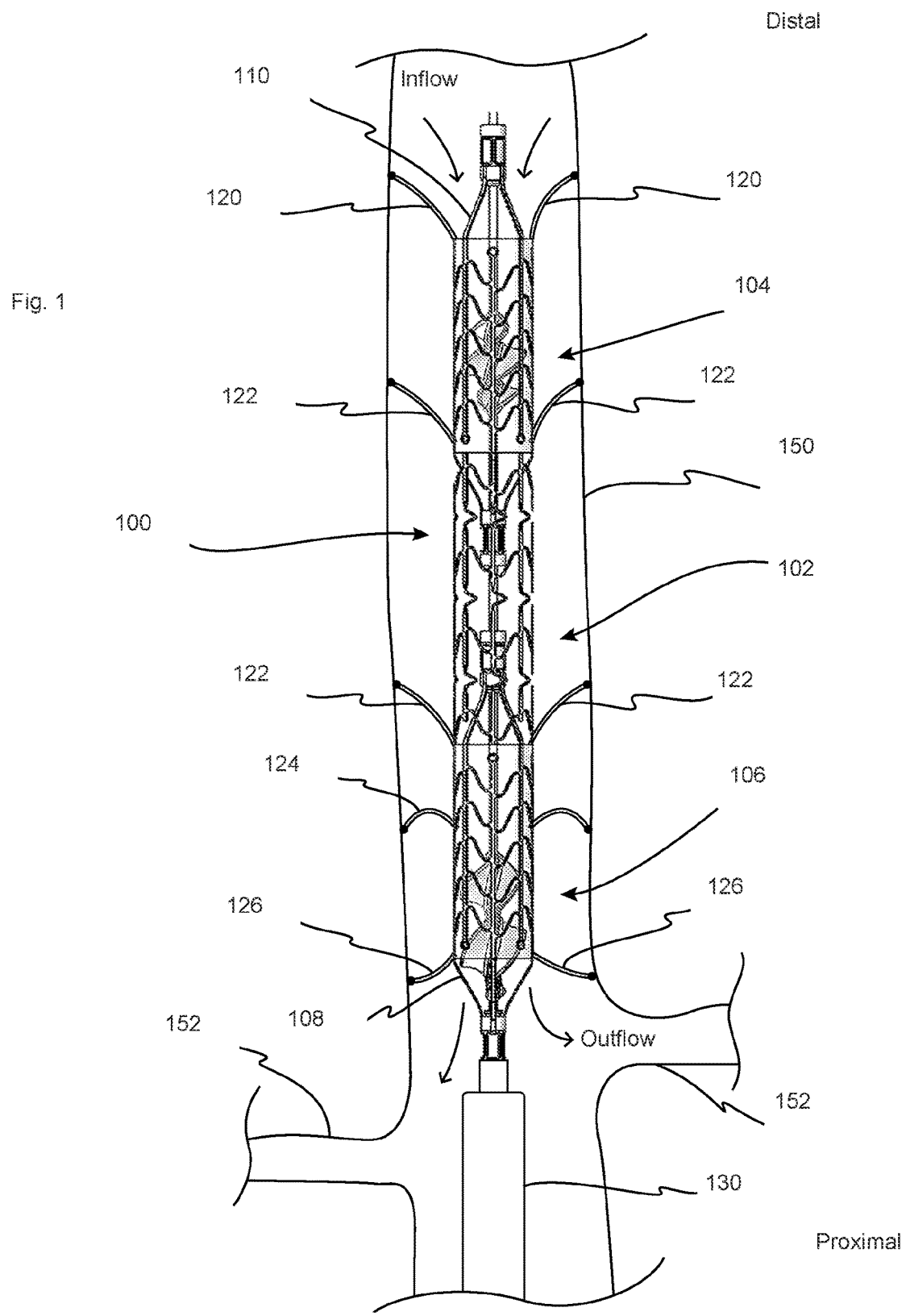
FIG. 1 is an example of an expandable pump portion secured in a descending aorta.
Figure 2:
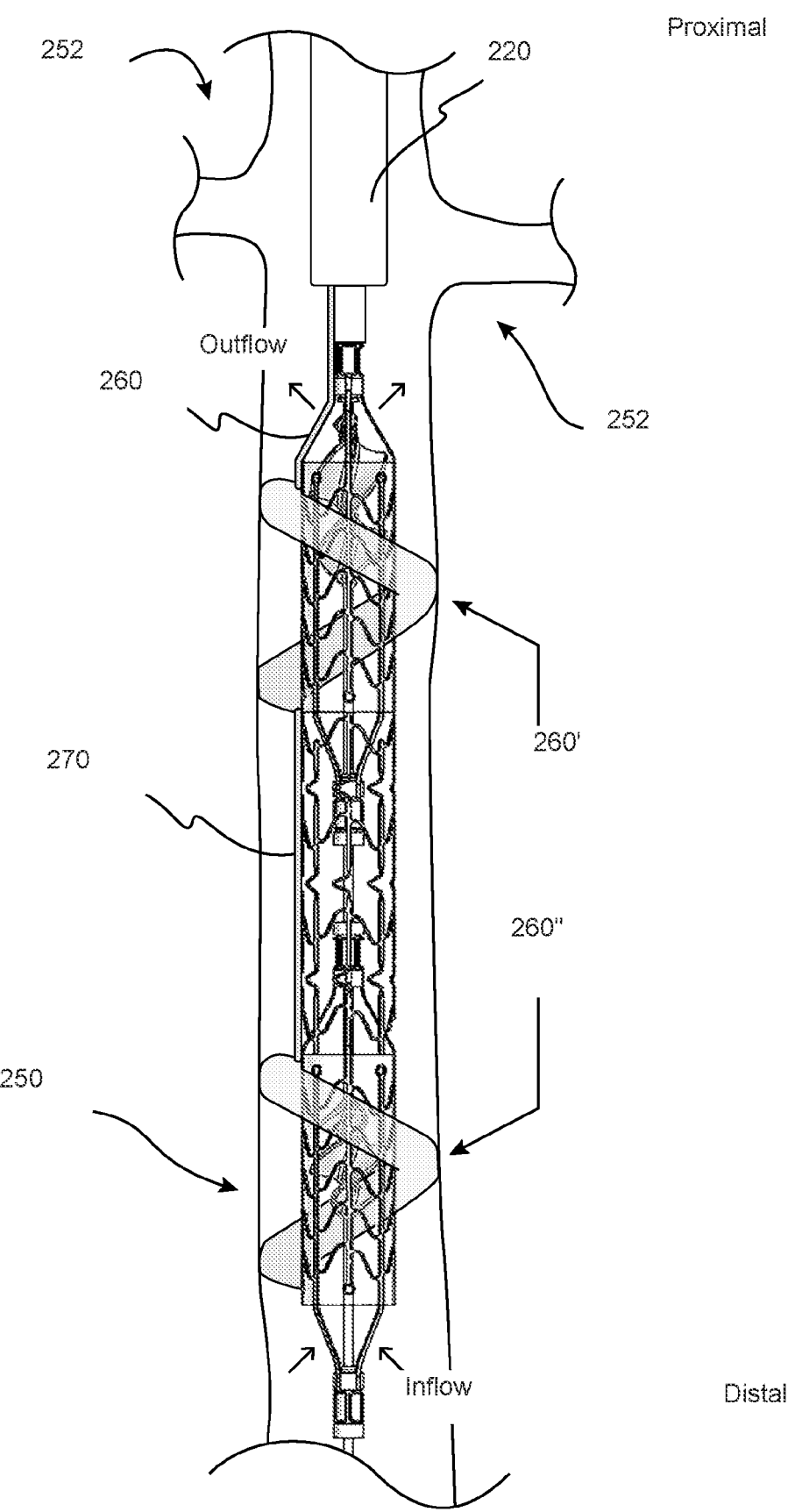
FIG. 2 is an example of an expandable pump portion with one or more inflatable anchors secured in a descending aorta.
Figure 3:
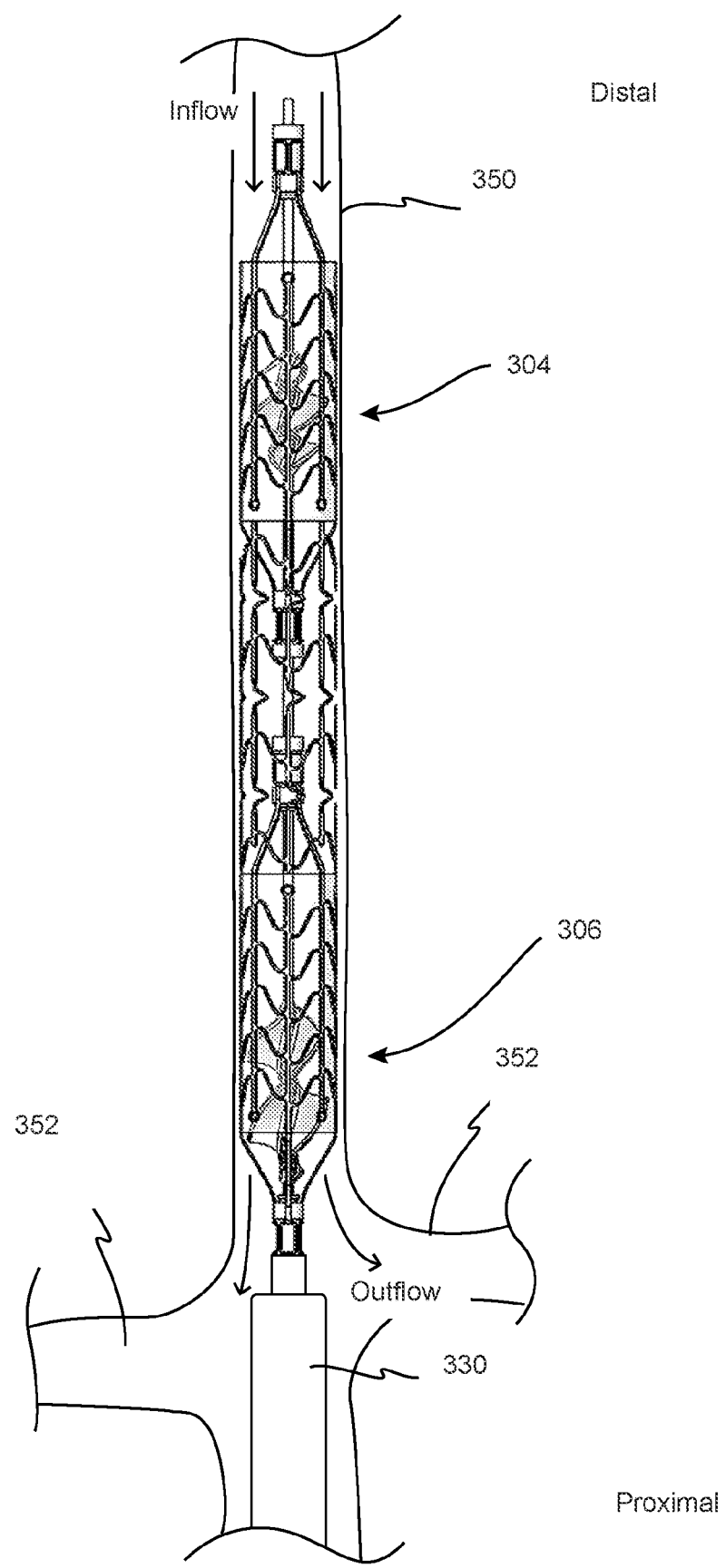
FIG. 3 is an example of an expandable pump portion secured in a descending aorta.

One aspect of the disclosure is related to intravascular multiple impeller blood pumps that include pump portions that are sized and configured for placement in the descending aorta, optionally within the abdominal aorta, such as is shown in the examples in FIGS. 1-3. The intravascular multiple impeller blood pumps may be configured for cardiovascular and circulatory support. The entirety of U.S. Pat. No. 9,572,915, including the background section thereof, is fully incorporated by reference herein in this context. For example, intravascular multiple impeller blood pumps herein may be used in cardiovascular support, and may be used to facilitate perfusion of targeted vessel and/or organs, such as the kidneys.

One aspect of the disclosure is related to intravascular multiple impeller blood pumps that include pump portions that are sized and configured for placement in an inferior vena cava ("IVC"). The background section of US 2017/0100527 is fully incorporated by reference herein in this context. For example, intravascular multiple impeller blood pumps herein may be placed in the vicinity of a junction of an IVC and one or more renal veins, and may be used to facilitate blood flow in the venous vasculature, optionally reduce renal venous pressure. Any of the disclosure in US 2017/0100527 related to delivery of a blood pump to a target location near the renal veins is incorporated by reference herein for all purposes, including any methods herein that include delivering a blood pump to a target location and/or expanding a blood pump at a target location. The disclosure in WO2018/226991A1, WO2019/094963 A1, WO2019/152875A1, WO2020/028537A1, WO2020/073047A1 may include exemplary multiple impeller blood pumps, any of which may be delivered, deployed, and operated to move fluid therethrough for cardiovascular and circulatory support according to any of the methods herein. In any of the relevant methods herein, a multiple impeller blood pump may be delivered to a location in a patient's descending aorta, such as in the abdominal aorta.

FIGS. 1-3 illustrate exemplary pump portions of multiple impeller blood pumps deployed in expanded configurations in the descending aorta, with the impellers shown expanded and rotating to pump blood through the blood conduit of the pump. The deployed and expanded pump portions shown in FIGS. 1-3 may be similar to the pump portions shown and described in WO2018/226991A1, WO2019/094963 A1, WO2019/152875A1, WO2020/028537A1, WO2020/073047A1, and any suitable disclosure in any of these publications incorporated fully by reference herein for all purposes may be incorporated by reference into the description of FIGS. 1-3 herein.

Figure 5:
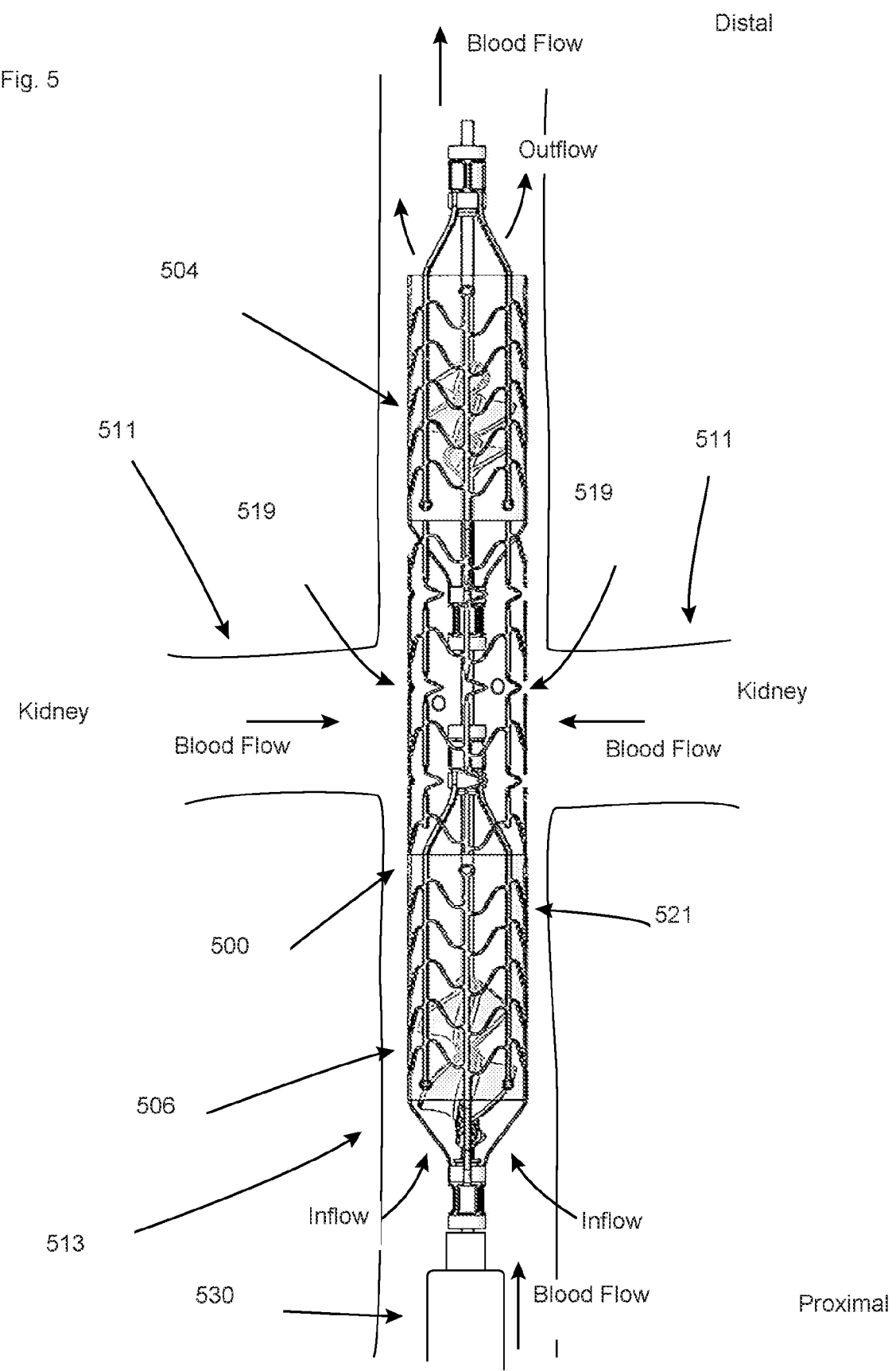
FIG. 5 is an example of an expandable pump portion secured in an inferior vena cava.

An exemplary advantage of the blood pumps and methods shown in FIGS. 1-3 is that the multiple impeller pump may be able to achieve higher flow rates than some existing single impeller blood pumps that are positioned in the descending aorta. The advantages of relatively low-profile and higher flow rate expandable blood pumps may be described in more detail in WO2018/226991A1, WO2019/094963 A1, WO2019/152875A1, WO2020/028537A1, WO2020/073047A1, and similarly apply to the relatively low-profile and higher flow rate blood pumps positioned for use in the descending aorta, such as those shown in FIGS. 1-3, or for use in a vena cava, such as shown in FIG. 5. For example, without limitation, the pump portions of the blood pumps herein may be sized and configured such that they can be introduced via a 10F introducer, while being able to achieve flow rates of at least 3.5 L/min when expanded and activated, which may be higher than some existing pump portions that are designed for placement in the descending aorta or vena cava.

Any of the blood pumps herein may include one or more anchors (which may also be referred to herein as stabilizing members) that are sized and configured to help stabilize a pump portion of the blood pump with respect to the descending aorta or IVC, examples of which are shown in FIGS. 1 and 2. To anchor or stabilize as used in this context refers generally to being anchored in the aorta (or IVC) to prevent axial migration of the pump relative to the aorta, although some minimal movement may still occur, such as due to slight deformation of one or more anchors when the pump is in use. FIG. 1 illustrates an exemplary pump portion 100 of a blood pump in an expanded configuration stabilized in place in descending aorta 150 and generally proximate to renal arteries 152, with most or all of pump portion 100 upstream the renal arteries. Pump portion 100 includes one or more anchors or stabilizing members (120, 122, 124, 126) that in their expanded configurations extends radially outward and optionally also distally from an expandable blood conduit or shroud 102 of the blood pump, as shown. Pump portion 100 may include one or more anchors, and any of those shown in FIG. 1 may be optional. For example, the pump may only have one or more distal stabilizing members 120 extending from a distal end or distal region of the expandable blood conduit, as shown. It may be desirable to have anchors at one or more ends or end regions of the pump, such as anchors 120 and anchors 126, and/or stabilizing members that are disposed axially between the fluid conduit ends, such as one or more of stabilizing members 122 or stabilizing members 124.

Any of the anchors or stabilizing members herein may comprise one or more materials such that the anchor is adapted to self-expand to an at least partially expanded configuration. For example, any of the anchors or stabilizing members herein may be adapted to self-expand after a sheath, and example of which is shown in FIG. 1 as sheath 130, is retracted proximally to allow the anchor(s) to expand. Any of the anchors herein may be re-sheathed before or after final pump deployment and activation if pump repositioning is needed, or if the pump is to be re-sheathed and removed from the patient, such as with sheath 130 shown in FIG. 1. Sheath 130 is adapted to be axially movable relative to the catheter and pump portions that are shown to deploy and sheath the expandable pump portion, which may be described in more detail in WO2018/226991A1, WO2019/094963 A1, WO2019/152875A1, WO2020/028537A1, WO2020/073047A1. Any of the anchors herein may comprises a deformable material, such as nitinol, and may be coupled to a scaffold section of the expandable pump portion. Coupled to in this context includes being integral with (e.g., unitary with) and being indirectly attached.

Anchors herein may have elongate finger or arm-like configurations, extending radially outward when deployed, such as exemplary anchors 120, 122, 124 and 126 shown in FIG. 1. Configurations in which they extend distally and radially relative to where they are coupled to the blood conduit, examples of which are shown in FIG. 1, may ease or facilitate the re-collapse and capture of the anchors when a sheath is advanced distally (relative motion) over the blood conduit and anchors.

The entirety of any of the anchors herein need not extend distally relative to the blood conduit to be able to facilitate collapse. For example, stabilizing members 124 may be considered to have a general curved, C, U, or bow shape when expanded, and initially extend radially and distally relative to the blood conduit, then extend further proximally at their radially outer ends as shown. When the sheath is advanced distally, stabilizing members 124 are adapted to be collapse and be re-sheathed. Additionally, any of the anchors herein may extend solely radially outward when expanded and will be able to be collapsed.

Any of the anchors herein may be separate components from the blood conduit (not unitary therewith), but may be secured to one or more other blood conduit components during manufacture. For example, any of the anchors herein may be secured to any portion of an expandable scaffold, examples of which are described in examples incorporated by reference herein. Anchors may optionally and alternatively be secured to and extend from a distal strut or a proximal strut of the expandable pump portion (not shown).

Anchors herein may be unitarily formed with one or more blood conduit components. For example, any of the anchors and scaffolds herein may be laser cut from the same nitinol tubular starting material. Forming the anchors unitarily with one or more blood conduit components may simplify construction by eliminating a step of coupling an anchor to a region of the blood conduit.

Any of the anchors herein may have distal free ends that are configured to further stabilize the anchor against tissue. For example, without limitation, any of the anchors herein may include an end that include one or more of barbs, protrusions, or any other type of element or configuration that is configured to increase the stability of the anchor with respect to the vessel wall, such as a descending aorta wall or IVC.

Any of the anchors herein may be equidistantly spaced apart around the shroud (circumferentially). For example, first and second anchors may be circumferentially spaced 180 degrees from each other, three anchors may be spaced 120 degrees from each other, four anchors may be spaced 90 degrees from each other, etc. In other embodiments, any of the anchors may not be circumferentially spaced equidistantly around the blood conduit.

FIG. 1 also shows exemplary distal expandable and collapsible struts 110, exemplary proximal expandable and collapsible struts 108, exemplary distal impeller 104, exemplary proximal impeller 106

Any of anchors herein may optionally be adapted to be inflatable, such as anchor 260' and 260" shown in the embodiment in FIG. 2. Any aspect of any other pump portion herein may be incorporated into the expandable pump portion shown in FIG. 2 (and vice versa), such as an expandable blood conduit, scaffold, membrane, impeller(s), and struts, examples of which are shown. Inflatable anchors 260' and 260" may be in fluid communication with inflation fluid in an inflation fluid source (not shown for clarity), which may be external to the patient. The pump portion in this embodiment has an inflatable anchor that comprises a distal inflatable anchor region 260" and a proximal inflatable anchor region 260', which are in fluid communication in this example with each other via an inflation line 270. Inflation lumen 260 is also in fluid communication with anchor region 260' and extends along one of the proximal struts and then proximally through the catheter portion of the blood pump, as shown in FIG. 2.

Any of the blood pumps herein may include an inflation lumen that extends to or towards an external portion of the blood pump, such as an external console or other external control portion of the pump. The inflation lumen may be in communication with an inflation fluid source, such as a gas source or a liquid source. One or more external pumps may help control the inflation of inflation fluid to the inflatable anchor(s). Inflation of the one or more inflatable anchors may occur at any time after the pump portion is deployed from a delivery sheath, such as sheath 220 as shown in FIG. 2. Any the inflatable anchors herein may be coupled to the expandable blood conduit using a wide variety to bonding concepts, such as spot welding or other techniques to couple inflatable members to an expandable blood conduit.

Any of the inflatable anchors herein may be configured to allow for some blood flow around the pump portion, before, during, and/or after operation of the pump. For example, any inflatable anchor herein may have an at least partially helical configuration when inflated, such as the anchor regions 260' and 260" shown in FIG. 2, which can allow blood to continue to flow around the expandable blood conduit without the inflatable element completely occluding blood flow in the descending aorta or IVC. FIG. 2 also shows renal arteries 252.

Any of the inflatable anchors herein may be sized and configured such that when inflated and expanded with a fluid, they expand and engage the descending aorta wall 250 and help anchor the pump in place to minimize axial migration of the blood conduit during use.

The outer dimension of any of the pump portions herein may be varied as needed for the implantation and/or the placement location within the patient. For example, the pump portion may be sized such that in an expanded configuration, an outer surface (optionally cylindrical) of the blood conduit directly engages or substantially engages a descending aorta or IVC sufficiently to anchor the pump in place and sufficiently minimize movement. An exemplary pump that is sized and configured to be expanded and anchored against a descending aorta 350 is shown in FIG. 3. The advantages of a multiple impeller pump apply in this embodiment, even if in this example the expandable pump portion is not collapsible to French sizes comparable to pump designs that have one or more anchors, for example. Any of the disclosure herein related to multi-impeller pumps is incorporated by reference into FIG. 3 and may be integrated into the example show in FIG. 3. FIG. 3 also illustrates exemplary distal impeller 304, proximal impeller 306, renal arteries 352 being perfused by the activated pump portion, and sheath 330 that can be used to deliver the expandable pump portion.

Exemplary descending aorta positions or locations for any of the pump portions herein are shown in FIGS. 1-3, with the pump portions positioned just upstream and proximate the ostia of the renal arteries, as shown. The position of the pump portions may be such that the proximal end of the blood conduit is aligned with, substantially aligned with, or just upstream, one or both of the ostia of the renal arteries. The outflow of the pump portions, as shown in FIGS. 1-3, may include a radial component. Positioning the pump just upstream to or aligned with one or both renal arteries may help direct blood towards or into the renal arteries, which may help perfuse the renal arteries and kidneys.

In alternative embodiments not shown in FIGS. 1-3, the multiple impeller pump portion is not expandable and collapsible. Non-expandable pumps may be positioned in the descending aorta as shown in any of FIGS. 1-3 just upstream to or aligned with a renal artery such that the pump outflow is still at least partially directed towards one or both renal arteries.

Figure 4:
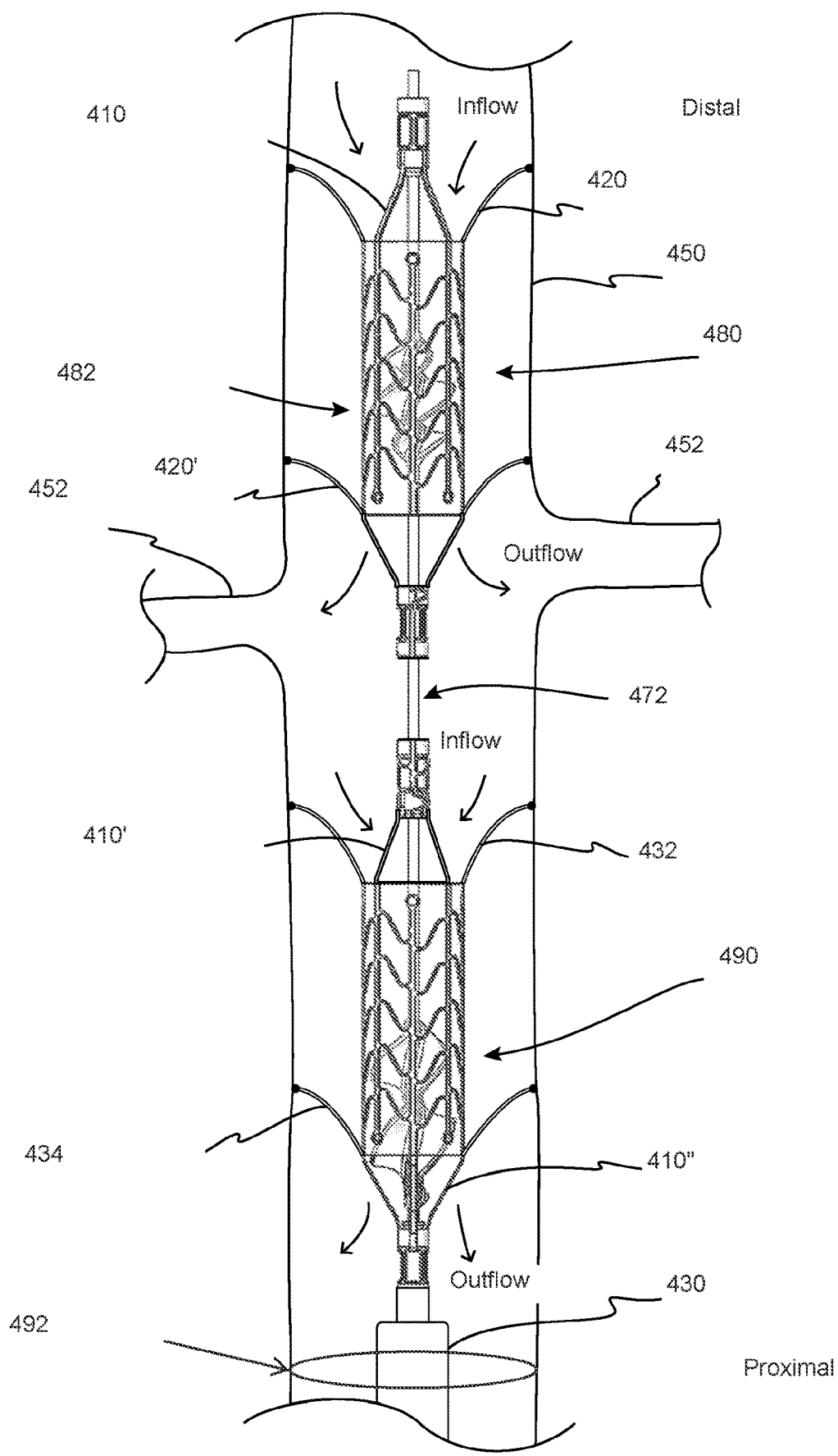
FIG. 4 is an example of an expandable pump portion secured in a descending aorta.

FIG. 4 illustrates an exemplary embodiment of a pump portion that is similar to the pump portions shown in FIG. 1-3, and applicable disclosure related to FIGS. 1-3 is incorporated by reference into the embodiment of FIG. 4. The blood pump shown expanded in place in FIG. 4 does not have a fluid conduit that extends all the way in between distal and proximal impellers, as shown. The pump portion in FIG. 4 includes a distal pump portion 480 that includes an expandable scaffold or basket, and a proximal pump portion 490 that includes an expandable scaffold or basket, each of which at least partially surrounds an impeller (distal impeller 482 is labeled). In this embodiment, the impellers may be rotated by the same or an otherwise common drive mechanism 472 (e.g., a drive cable or drive shaft), which may be rotated by an external motor that is also in rotational communication with the impellers. The distal pump portion 480 includes a distal blood conduit with an inflow and an outflow as shown, and the proximal pump portion 490 includes a proximal blood conduit with an inflow and an outflow as shown. The blood conduits may each include a scaffold coupled to a membrane. The central region between the distal pump portion 480 and the distal pump portion 490 is open and does not include a blood conduit, which allows blood pumped by the distal pump portion 480 to perfuse the renal arteries, as shown by the outflow of the distal pump portion 480. The proximal pump portion 490 pumps blood towards the lower region of the body, as shown. The distal pump portion 480 is shown positioned just upstream to the renal arteries 452, but the proximal end of the distal blood conduit may also be substantially aligned with one or more renal arteries so the outflow aids to perfuse one or both renal arteries. Exemplary anchors 420, 420', 432 and 434 are also shown, which may be sized and configured to expand and contact the descending aorta 450 to anchor the pump portion in the ascending aorta.

The pump portion in FIG. 4 may alternatively or in addition to incorporate any suitable feature described with respect to the embodiments in FIGS. 1-3. For example, a variation of the pump shown in FIG. 4 includes one or more inflatable anchors, such as those shown in FIG. 2, to help anchor the pump portion in the descending aorta. Alternatively, the embodiment in FIG. 4 may be sized such that outer surfaces (e.g., cylindrical surfaces) of one or both of pump portions 480 and 490 expand into direct contact with descending aorta tissue 450, such as is the case in the embodiment shown in FIG. 3. This is an example of suitable features from any of the embodiments herein being combined with suitable features of any of the other embodiments herein.

In a variation on the blood pump shown in FIG. 4, a proximal portion of the distal impeller extends to some extent proximally beyond the proximal end of the distal blood conduit, as is shown with the relative positions of the proximal impeller in FIGS. 1-3. This may cause the outflow from the distal pump portion 480 to have more of a radial component than distal pump portions in which the distal impeller does not extend proximally beyond the proximal end of the blood conduit. This may help perfuse the renal arteries to a greater extent by directing more of the outflow from the distal pump portion radially outwards towards the ostia of the renal arteries.

In a variation of the blood pump of FIG. 4, the proximal pump portion 490 may include an impeller that is adapted and configured such that when the impeller is rotated, the impeller causes the proximal pump portion 490 to pump blood in a retrograde direction opposite that of the normal flow of blood, which is upward or in a superior direction in FIG. 4. In this variation, the proximal pump portion 490, when activated, pumps blood in a retrograde direction towards the ostia of the renal arteries rather than pumping blood downstream. In these variations, the impellers may be driven by a common drive mechanism 472 (e.g., a drive cable and/or drive shaft). In some methods of use, the operation of the impellers in this variation may be controlled in a manner related to the cardiac cycle of the heart. In some uses, for example, the impellers may be activated synchronously with the cardiac cycle. For example without limitation, the distal and proximal impellers can be turned on or activated during systole or a portion of systole (e.g., peak systole), and deactivated during diastole or a portion of diastole. Controlling pump operation in this exemplary manner may help perfuse the renal arteries during systole.

FIG. 4 also illustrates optional occluding member 492. Occluding member 492 may be controllably inflated and deflated to controllably occlude blood flow through the descending aorta in the vicinity of the pump portion in coordination with the cardiac cycle to help perfuse the kidneys. With respect to the original description of FIG. 4 in which both impellers pump blood in an antegrade direction when rotated, the blood pump may include an optional inflatable and deflatable occluding member 492. The occluding member may be coupled to sheath 430 as shown, but in alternative embodiments it may be secured to the catheter shaft. The inflatable and deflatable member 492 may be coupled to an outer surface of the sheath or the catheter shaft, and may be in fluid communication with a fluid source external to the patient via an inflation pathway extending through the catheter. In some embodiments, the occluding member 492 may be controllably inflated to occlude blood flow downstream the occluding member during systole to help perfuse the kidneys, and may be controllably deflated during diastole to allow blood to flow downstream.

An aspect of this disclosure is related to intravascular blood pumps with pump portions that are sized and configured for placement in the vicinity of the junction of an inferior vena cava ("IVC") and one or more renal veins, and operated to reduce renal venous pressure. For example, in variations on FIGS. 1-4, the blood pump may instead be positioned on the venous side of the vasculature so the pump portion is delivered and deployed in an IVC. FIG. 1-4 may be modified such that the renal arteries are labeled as renal veins, the descending aorta is an IVC, and the natural blood would flow out of the renal veins, into the IVC, and in a superior direction back towards the heart.

FIG. 5 illustrates an exemplary pump portion 500 of an exemplary blood pump that may be include any suitable aspect of any of the blood pump described herein, and which may include any suitable structural component of any blood pump herein, including any of those shown in FIG. 1-4. For example, pump portion 500 may be sized to expand and contact at least a portion of an IVC wall 513. Additionally, the pump portion in the embodiment of FIG. 5 may include one or more anchoring/stabilizing members adapted to expand radially outward from the blood conduit and engage an IVC wall. FIG. 5 shows the pump portion 500 positioned in an IVC 513, with the distal impeller 504 positioned superior to the renal veins 511, and a proximal impeller 506 positioned inferior to the renal veins 511. Relative positions of kidneys is also labeled.

The impellers 504 and 506 are configured to pump blood from the pump inflow, through the expanded blood conduit or shroud 521, and toward the pump outflow, as shown. One or more of the drive shaft rotation direction or impeller configuration causes the blood to be pumped in this direction through the expandable blood conduit 521.

In this exemplary embodiment, as shown in FIG. 5, the blood pump includes one or more flow controllers 519 that are positioned, sized and configured to facilitate the flow of blood from outside the blood conduit and into the blood conduit. The pump portion 500 is expanded in a position such that the one or more flow controllers 519 (shown generally as circular or oval in this embodiment) are positioned generally at the location of the renal veins, such that blood flow out of the veins may enter into the blood pump fluid conduit through the one or more flow controllers. For example without limitation, any of the one or more flow controllers may comprise an opening, or in some embodiments any of the flow controllers herein may include a one-way valve (e.g., check valves) that allow blood to pass into the blood conduit but not out of the blood conduit. Other types of suitable flow controllers may of course be incorporated into the pump portions herein. One or more flow controllers may be axially spaced (along the length of the pump portion) from other flow controllers. Flow controllers may be disposed circumferentially around a periphery of the blood conduit at any distance apart. For example, one or more flow controllers may be spaced 30 degrees, 60 degrees or 90 degrees apart. In any of the blood pumps herein, one or more flow controllers may not be circumferentially or axially spaced at regular intervals. In any of these embodiments, there may be from one—twenty separate flow controllers, such as from two to ten. FIG. 5 also shows exemplary delivery sheath 530.

In an alternative to that shown in FIG. 5, a pump portion with multiple impellers may be expanded in place at a location that is superior to both veins, similar to the superior placement of the pump portion relative to the renal arteries shown in FIG. 1. In these alternatives, the blood conduit would be downstream the renal veins, as opposed to only a portion of the pump portion being downstream as shown in FIG. 5.

With respect to any of the methods herein that position a pump portion in the arterial vasculature, such as in the embodiments in FIGS. 1-4, the blood pump may be percutaneously and trans-luminally delivered to a portion of the descending aorta or renal artery of the patient via a femoral artery of the patient, for example, although other known entry locations and access pathways may also be used to deliver the pump portion to the target anatomy.

With respect to any of the methods herein that position a pump portion in the venous vasculature, such as in the embodiments in FIG. 5, the blood pump may be percutaneously and trans-liminally delivered to a portion of the or renal vein of the patient via a femoral vein, for example, although other known entry locations and access pathways may also be used to deliver the pump portion to the target anatomy, such as via a subclavian vein or jugular vein, for example. It is understood that the terms distal and proximal are used herein as is common to refer to the relative directions based on the pathway in which the blood pump is advanced, examples of which are shown in FIGS. 1-5.

In alternative embodiments, any of the pump portions herein may be positioned in a renal artery rather than in a descending aorta. For example, the pump portion may be delivered via a femoral artery and then advanced into a renal artery, optionally over a guidewire that has been previously advanced into a right or left renal artery. Similarly, any of the pump portions herein may be positioned in a renal vein rather than in an IVC. For example, the pump portion may be delivered via, a femoral vein and then advanced into a renal vein, optionally over guidewire that has been advanced into a right or left renal vein. In any of these embodiments, pump portions from separate blood pumps can be positioned bilaterally in first and second renal arteries, or in first and second renal veins, or in any combination of renal arteries and renal veins (e.g., up to four pump portions delivered through separate sheaths). In any of these alternative embodiments, a pump portion positioned in a renal vein or a renal artery may optionally be a single impeller pump rather than a multiple impeller pump.

The invention claimed is:

1. A method of supporting circulation in a descending aorta of a subject, comprising:
advancing an expandable pump portion of a blood pump into a descending aorta of a subject, the pump portion comprising an expandable blood conduit comprising a scaffold coupled to a membrane between a pump inflow and a pump outflow, the pump portion further including first and second expandable impellers at least partially within the blood conduit;
expanding the expandable blood conduit to an expanded and deployed configuration within the descending aorta;
expanding the first expandable impeller into an expanded configuration at least partially within the blood conduit;
expanding the second expandable impeller into an expanded configuration at least partially within the blood conduit and having a portion that extends beyond the expandable blood conduit; and
rotating the first and second expandable impellers to thereby move blood into the pump portion, through the blood conduit, and out of the pump portion, wherein rotation of the portion of the second expandable impeller that extends beyond the expandable blood conduit causes the pump outflow to include a radial flow component.

2. The method of claim 1, wherein the rotating step moves blood through the blood conduit at a rate of at least 3.5 L/min.

3. The method of claim 1, wherein moving blood out of the pump outflow perfuses at least one renal artery.

4. The method of claim 1, wherein expanding the expandable blood conduit comprises expanding the expandable blood conduit to a deployed configuration within the descending aorta such that the pump outflow is upstream or aligned with a renal artery, and wherein the outflow is at least partially directed radially into the renal artery due to the position of the blood conduit in the descending aorta.

5. The method of claim 1, wherein expanding the expandable blood conduit to a deployed configuration within the descending aorta comprises expanding the expandable blood conduit to a deployed configuration near a renal artery such that the pump outflow perfuses at least one renal artery.

6. The method of claim 1, wherein expanding the expandable blood conduit within the descending aorta comprises expanding a distal scaffold to an expandable configuration that provides radial support to the blood conduit at the location of the first impeller.

7. The method of claim 6, wherein expanding the expandable blood conduit within the descending aorta comprises expanding a proximal scaffold to an expandable configuration that provides radial support to the blood conduit at the location of the second impeller.

8. The method of claim 1, wherein expanding the expandable blood conduit comprises expanding a central region of the blood conduit that is between the first and second impellers, wherein the central region is more flexible than regions of the blood conduit that surround the first and second impellers.

9. The method of claim 1, wherein expanding the expandable blood conduit to a deployed configuration within the descending aorta comprises expanding the expandable blood conduit to a deployed configuration within the descending thoracic aorta.

10. A method of supporting circulation in a descending aorta of a subject, comprising:
advancing an expandable pump portion of a blood pump into a descending aorta of a subject, the pump portion including a distal impeller and a proximal impeller;
expanding a distal expandable blood conduit comprising a scaffold coupled to a membrane into an expanded configuration aligned with or upstream to a renal artery;
expanding the distal impeller to an expanded configuration at least partially within the distal expandable blood conduit and having a portion that extends beyond the distal expandable blood conduit;
expanding a proximal expandable blood conduit into an expanded configuration downstream from the renal artery;
expanding the proximal impeller to an expanded configuration at least partially within the proximal expandable blood conduit;
rotating the distal impeller to move blood into a distal end of the distal expandable blood conduit, through the distal expandable blood conduit, and out of a proximal end of the distal expandable blood conduit, the portion of the distal impeller extending beyond the distal expandable blood conduit causing blood moving out of the distal expandable blood conduit to include a radial flow component; and
rotating the proximal impeller to move blood through the proximal expandable blood conduit.

11. The method of claim 10, wherein rotating the distal impeller causes blood to move out of the proximal end of the distal expandable blood conduit and perfuse the renal artery, optionally also perfusing a second renal artery.

12. The method of claim 10, wherein rotating the distal and proximal impellers moves blood past the distal and proximal impellers in an antegrade direction.

13. The method of claim 10, wherein rotating the distal impeller moves blood past the distal impeller in an antegrade direction, and wherein rotating the proximal impeller moves blood past the proximal impeller in a retrograde direction toward the renal artery.

14. The method of claim 13, wherein rotating the distal and proximal impellers is performed discontinuously and in a manner that is related to one or more aspects of the subject's cardiac cycle.

15. The method of claim 14, wherein rotating the distal and proximal impellers occurs during at least a portion of systole, and wherein the distal and proximal impellers are not rotated during at least a portion of diastole, optionally during any of diastole.

16. The method of claim 10, wherein rotating the proximal impeller moves blood into a distal end of the proximal expandable blood conduit, through the proximal expandable blood conduit, and out of a proximal end of the proximal expandable blood conduit.

17. The method of claim 10, wherein expanding a distal expandable blood conduit into an expanded configuration aligned with or upstream to a renal artery comprises expanding a distal expandable scaffold.

18. The method of claim 10, wherein expanding a proximal expandable blood conduit comprises expanding a proximal expandable scaffold.

* * * * *